United States Patent [19]

Schaub et al.

[11] 4,074,056

[45] Feb. 14, 1978

[54] 3-ALKYL-2-(6-CARBOXYHEXYL) CYCLOPENTANONES AND ESTERS AND SALTS THEREOF

[75] Inventors: Robert Eugene Schaub, Upper Saddle River, N.J.; Karel Francis Bernady, Suffern, N.Y.; Martin Joseph Weiss, Oradell, N.J.

[73] Assignee: American Cyanamid Company, Stamford, Conn.

[21] Appl. No.: 756,667

[22] Filed: Jan. 4, 1977

Related U.S. Application Data

[60] Division of Ser. No. 240,814, April 3, 1972, Pat. No. 4,018,811, which is a continuation-in-part of Ser. No. 225,680, Feb. 11, 1972, abandoned, which is a continuation-in-part of Ser. No. 95,910, Dec. 7, 1970, abandoned.

[51] Int. Cl.$^2$ ............................................. C07C 177/00
[52] U.S. Cl. ................................. 560/51; 260/514 D; 260/515 R; 424/305; 424/308; 424/317; 560/121
[58] Field of Search ................... 260/468 D, 473, 514, 260/515, 469

[56] References Cited

PUBLICATIONS

Finch et al., J. Org. Chem., 36, 3191 (1971).

*Primary Examiner*—Robert Gerstl
*Attorney, Agent, or Firm*—Edward A. Conroy, Jr.

[57] ABSTRACT

This disclosure describes compounds of the class of substituted 9-oxoprostanoic acids and the esters and cationic salts thereof, useful as antimicrobial agents, hypotensive agents, anti-ulcer agents, or as intermediates, and novel processes for preparing the same.

10 Claims, No Drawings

3-ALKYL-2-(6-CARBOXYHEXYL) CYCLOPENTANONES AND ESTERS AND SALTS THEREOF

CROSS REFERENCE TO RELATED APPLICATION

This is a division of application Ser. No. 240,814, filed Apr. 3, 1972 now U.S. Pat. No. 4,018,811 Which in turn is a continuation-in-part of our copending application Ser. No. 225,680, filed Feb. 11, 1972 now abandoned which in turn is a continuation-in-part of our copending application Ser. No. 95,910, filed Dec. 7, 1970. now abandoned.

BRIEF SUMMARY OF THE INVENTION

This invention n to new organic compounds and, more particularly, is concerned with substituted 9-oxoprostanoic acids [3-alkyl-2-(ω-carboxyalkyl)cyclopentanones] and esters thereof which may be represented by the following general formula:

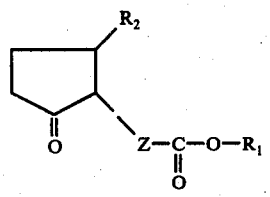

wherein $R_1$ is hydrogen or lower alkyl $R_2$ is a straight chain alkyl group having from 1 to 10 carbon atoms, inclusive; and Z is a divalent radical selected from the group consisting of

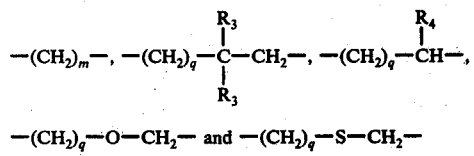

wherein m is an integer from 4 to 8, inclusive, q is an integer from 3 to 5, inclusive, $R_3$ is lower alkyl, and $R_4$ is lower alkyl, fluoro or phenyl. Suitable lower alkyl groups contemplated by the present invention are those having up to four carbon atoms such as, for example, methyl, ethyl, isopropyl, sec-butyl, etc. The straight chain alkyl groups contemplated by the present invention are methyl, ethyl, n-propyl, n-butyl, n-amyl, n-hexyl, n-heptyl, n-octyl, n-nonyl and n-decyl.

DETAILED DESCRIPTION OF THE INVENTION

Also embraced within the scope of the present invention are the non-toxic, pharmaceutically acceptable salts of the substituted 9-oxoprostanoic acids [3-alkyl-2-(ω-carboxyalkyl)cyclopentanones]. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel substituted 9-oxoprostanoic acids and esters thereof of the present invention are obtainable as yellow oils having characteristic absorption spectra. They are relatively insoluble in water but are relatively soluble in common organic solvents such as ethanol, ethyl acetate, dimethylformamide, and the like. The cationic salts of the substituted 9-oxoprostanoic acids are, in general, white to yellow crystalline solids having characteristic melting points and absorption spectra. They are relatively soluble in water, methanol, and ethanol but are relatively insoluble in benzene, diethyl ether, and petroleum ether.

The prostaglandins are a family of closely related compounds which have been obtained from various animal tissues, and which stimulate smooth muscle, lower arterial blood pressure, antagonize epinephrine-induced mobilization of free fatty acids, and have another pharmacological and autopharmacological effects in mammals. See Bergstrom et al., J. Biol. Chem. 238, 3555 (1963) and Horton, Experientia 21, 113 (1965) and references cited therein. All of the so-called natural prostaglandins are derivatives of prostanoic acid:

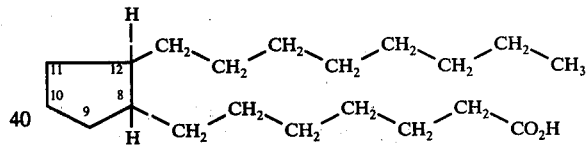

The hydrogen atoms attached to C-8 and C-12 are in trans configuration.

The novel compounds of the present invention may be readily prepared from 2-carbethoxycyclopentanone in accordance with the reaction schemes set forth in Flowsheets A through G. In particular, the requisite 2-(ω-carbethoxyalkyl)cyclopent-2-en-1-one intermediates (VIII) may be prepared in accordance with the following reaction scheme:

FLOWSHEET A

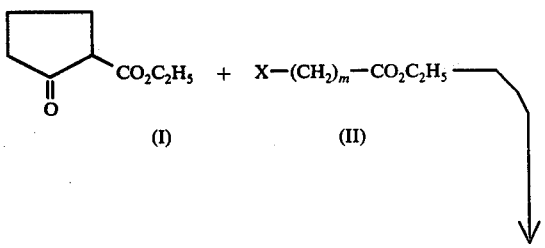

FLOWSHEET A

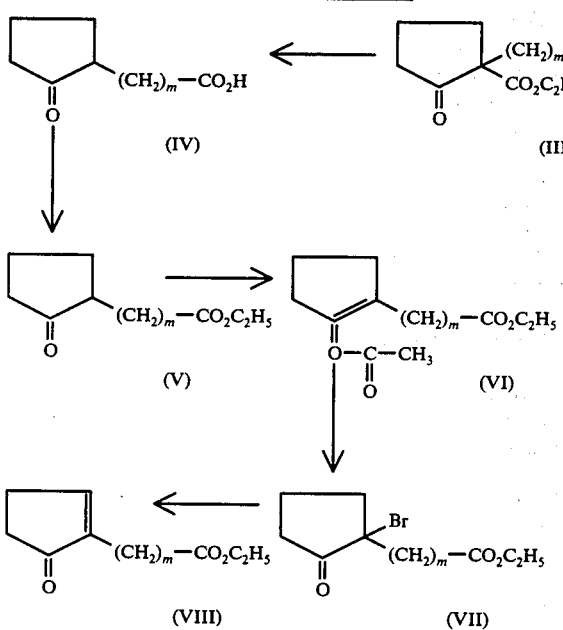

wherein m is as hereinabove defined and X is iodo or bromo. In accordance with this reaction scheme, the cyclopent-2-en-1-ones (VIII) are developed by first converting 2-carbethoxycyclopentanone (I) to the sodium enolate thereof by means of sodium hydride in dimethoxyethane and then treating the sodium enolate with an ethyl ω-haloalkanoate (II). There is thus obtained the corresponding 2-carbethoxy-2-(ω-carbethoxyalkyl)cyclopentanone (III) which is then hydrolyzed and decarboxylated to afford the 2-(ω-carboxyalkyl)cyclopentanone (IV). This acid is then esterified with ethanol whereby the 2-(ω-carbethoxyalkyl)cyclopentanone (V) is obtained. The reaction conditions for carrying out the above sequence of reactions are well known in the art. The conversion of the cyclopentanone (V) to the enol acetate (VI) is effected by heating with acetic anhydride in the presence of p-toluenesulfonic acid. Preparation of the enol acetate (VI) usually requires heating for a period of from about 8 to 36 hours. During this period, it is preferable to allow by-product acetic acid to distill out in order to force the reaction to completion. The bromination of the enol acetates (VI) to the 2-bromocyclopentanones (VII) is preferably carried out in a two phase system as follows. A solution of bromine in chloroform is added to a rapidly stirred mixture of a solution of the enol acetate (VI) in chloroform and an aqueous solution of an acid acceptor such as calcium carbonate or soda ash. This addition is carried out at 0°–5° C. over a period of about half an hour, stirring is continued for an additional period of about half an hour to a few hours, and the product VII) is then isolated by standard procedures. The dehydrobromination of the 2-bromocyclopentanones (VII) is preferably carried out in dimethylformamide with a mixture of lithium bromide and lithium carbonate at the reflux temperature for a period of about 30 minutes to an hour or so. The so formed cyclopent-2-en-1-ones (VIII) are also isolated by standard procedures well known in the art. Substitution of X—$(CH_2)_q$—$C(R_3)_2$——$CH_2$—$CO_2C_2H_5$ for (II) in Flowsheet A and carrying through the sequence of transformations illustrated therein is productive of the following cyclopent-2-en-1-one (VIIIa):

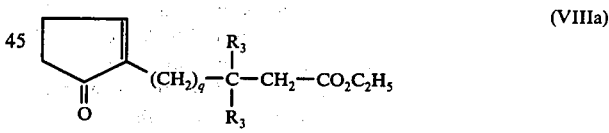

(VIIIa)

wherein X, q and $R_3$ are as hereinabove defined.

The required cyclopent-2-en-1-one intermediates of general structure (XVI), wherein in the side-chain has a lower alkyl group, fluorine atom or phenyl group alpha to the carbethoxy function, may be prepared in accordance with the following reaction scheme:

FLOWSHEET B

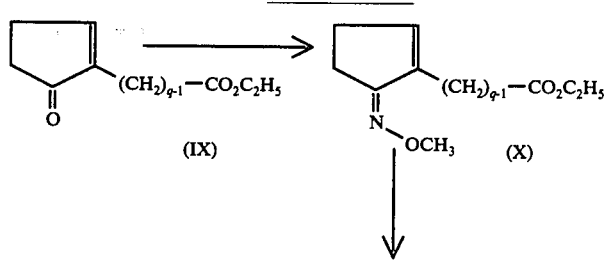

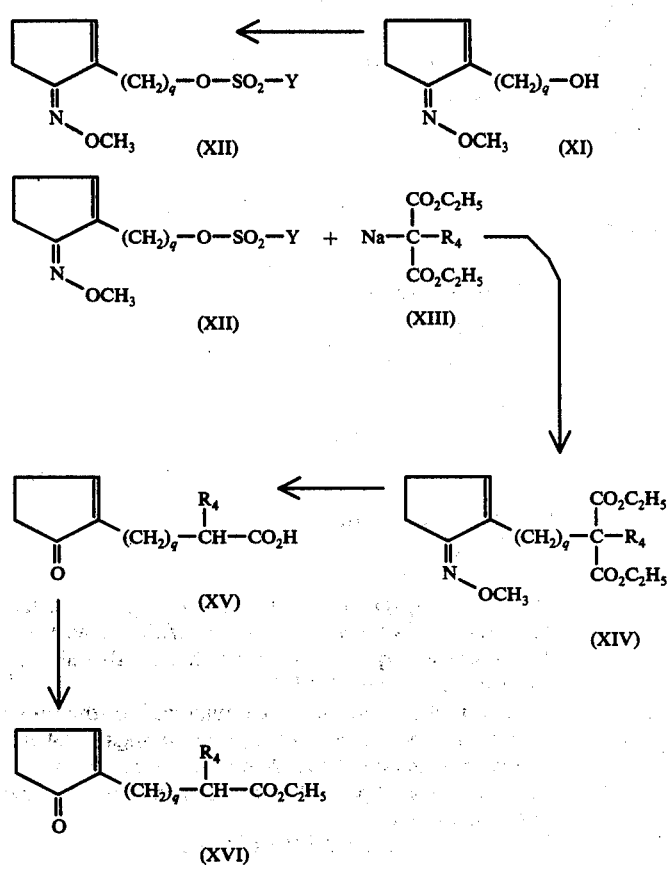

wherein $q$ and $R_4$ are as hereinabove defined, and Y is a methyl or p-tolylradical. In accordance with this reaction scheme, the 2-(ω-carbethoxyalkyl)cyclopent-2-en-1-ones (IX), prepared as described in Flowsheet A for the preparation of (VIII) where $m$ is 2-4, inclusive, are converted to the corresponding 1-methoximino-2-(ω-carbethoxyalkyl)-2-cyclopentenes (X) by treatment with methoxyamine. With the ring carbonyl function thus blocked it is possible to effect a preferential reduction of the ester group by treatment with diisobutylaluminum hydride. The resulting alcohol (XI) is converted to a mesylate or tosylate derivative (XII), which undergoes displacement on treatment with the sodium salt of a diethyl substituted malonate (XIII) to provide the disubstituted malonate derivatives (XIV). Hydrolysis and decarboxylation as well as concomittant cleavage of the methoximino blocking group provides the desired 2-(ω-carboxy-α-substituted alkyl)cyclopent-2-en-1-ones (XV), which are readily converted to the corresponding ester (XVI) by the usual Fisher procedure.

The requisite 2-(ω-carbethoxy-3-oxa-alkyl)cyclopent-2-en-1-ones (XXII) and 2-(ω-carbethoxy-3-thia-alkyl)-cyclopent-2-en-1-ones (XXVI) may be prepared in accordance with the reaction schemes of Flowsheet C, wherein $q$ is as hereinbefore defined.

FLOWSHEET C

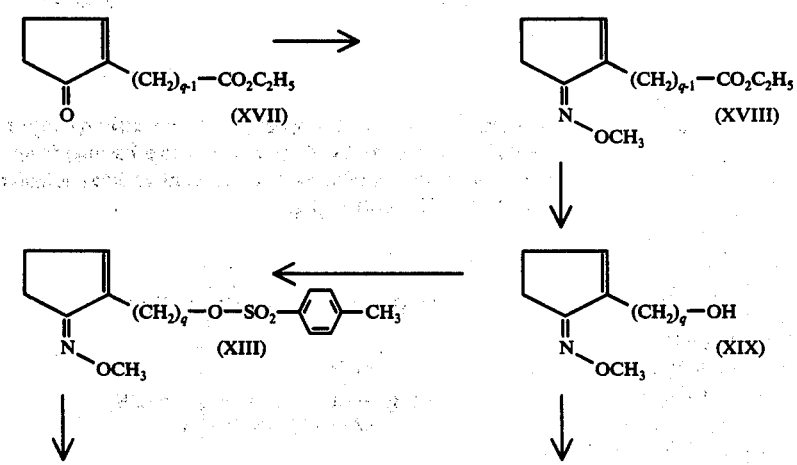

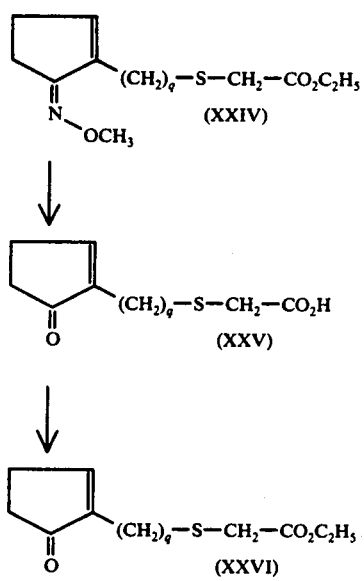 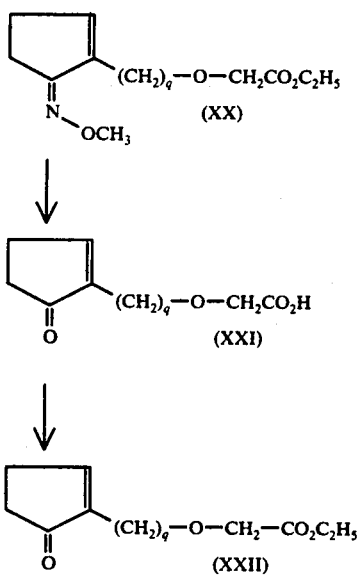

In accordance with the reaction scheme shown in Flowsheet C, for the preparation of the oxa derivatives (XXII), an appropriate 2-(ω-carbethoxyalkyl)cyclopent-2-en-1-one (XVII) is converted to the corresponding methoxime (XVIII), the ester function of which is then preferentially reduced with diisobutylaluminum hydride to afford the methoxime alcohol (XIX). The alcohol (XIX) is converted on treatment with n-butyl lithium to the lithio alcoholate, which then is O-alkylated by reaction with ethyl bromoacetate to provide (XX). Hydrolysis with acetone-aqueous hydrochloric acid furnishes the deblocked keto-acid (XXI), which is the re-esterified with ethanol in the presence of p-toluenesulfonic acid to give the required 2-(ω-carbethoxy-3-oxa-alkyl)cyclopent-2-en-1-one (XXII). O-Alylation can also be accomplished by treatment of the lithio alcoholate of (XIX) with sodium or other metal salt of bromoacetic acid, in which case the free carboxylix acid corresponding to ester (XX) is obtained. Hydrolysis as for (XX) provides the keto acid (XXI).

The preparation of the thia derivatives (XXVI), proceeds from the intermediate alcohol (XIX), which after conversion to the tosylate intermediate (XXIII) and reaction with the sodium salt of ethyl mercaptoacetate furnishes intermediate (XXIV). Deblocking of XXIV with acetone-aqueous hydrochloric acid provides the keto-acid (XXV), which on re-esterification with ethanol gives the required 2-(ω-carbethoxy-3-thia-alkyl)cyclopent-2-en-1-ones (XXVI).

Certain of the intermediate compounds of the present invention may be obtained by the conjugate 1,4-addition of an alanate salt to a 2-substituted cyclopent-2-en-1-one. This novel procedure is set forth in the following reaction scheme:

FLOWSHEET D

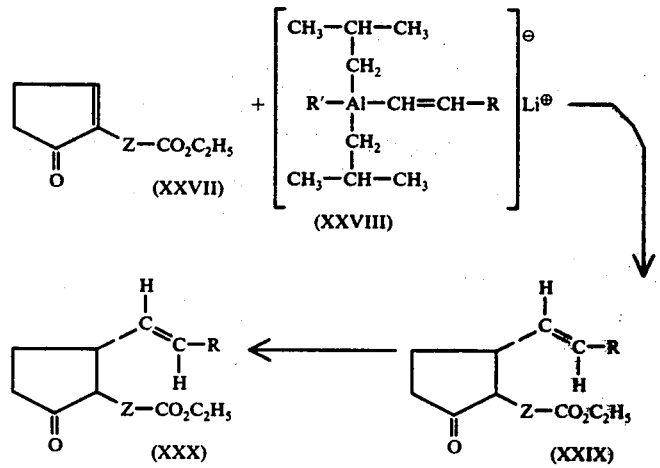

wherein R' is a lower alkyl group, preferably methyl or n-butyl, R is a straight chain alkyl group having from 1 to 8 carbon atoms, and Z' is a divalent radical selected from the group consisting of

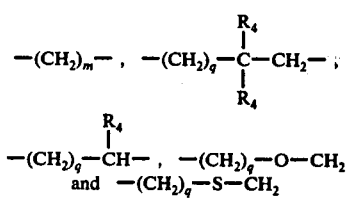

wherein m and q are as hereinabove defined and R₄ is a lower alkyl radical. The compounds (XXIX) are readily prepared by the conjugate 1,4-addition of an alanate salt (XXVIII) to a 2-substituted cyclopent-2-en-1-one (XXVII). The yields for this operation are usually high and a clean product, uncontaminated with 1,2-addition product, is usually obtained. Furthermore, the transfer of the alkene group is effected with retention of the trans-configuration of the hydrogen atoms attached to the double bond, and no reaction is noted at the carbethoxy function of (XXVII). Another noteworthy aspect of this reaction is that it does not require a catalyst. The alanate salts (XXVIII) are conveniently prepared by the reaction of an appropriate 1-alkyne (R—CaCH) with diisobutylaluminum hydride, followed by reaction with a lower alkyl lithium derivative, preferably methyl lithium or n-butyl lithium. Suitable 1-alkynes which may be thus employed are, for example, 1-propyne, 1-butyne, 1-pentyne, 1-hexyne, 1-heptyne and 1-octyne. The reaction of the 1-alkyne with diisobutylaluminum hydride cleanly provides the trans-double bond and is preferably carried out in an inert solvent such as benzene, toluene, and the like at temperatures in the range of 40°-60° C. for several hours. The solvent is removed in vacuo and the subsequent reaction with methyl or n-butyl lithium is preferably carried out in an ether-type solvent such as diethyl ether, dibutyl ether, tetrahydrofuran, and the like. This reaction is rapid and is preferably carried out at 0°-10° C. with cooling. The conjugate 1,4-addition of the resulting alanate salt (XXVIII) to the cyclopent-2-en-1-one (XXVII) is preferably carried out at ambient temperatures for a period of 12 to 24 hours. This reaction is also best carried out in an ether-type solvent such as diethyl ether, dibutyl ether, tetrahydrofuran, and the like. The intermediate alanate-enolate adduct is then hydrolyzed in situ with dilute hydrochloric acid with cooling, and the products (XXIX) are isolated in the usual manner well known in the art. The conversion of the esters (XXIX) to the acids (XXX) is readily accomplished by mild saponification procedures such as in 0.5N aqueous-methanolic KOH at room temperature for 20-48 hours.

The novel compounds of the present invention may be readily prepared by the conjugate 1,4-addition of a Grignard reagent (XXXII) to a lower alkyl ester of a 2-(ω-carboxyalkyl)cycylopent-2-en-1-one (XXXI) in accordance with the following reaction scheme:

FLOWSHEET E

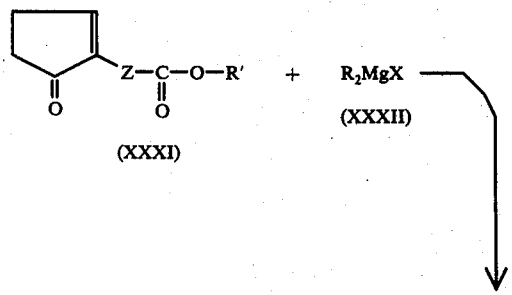

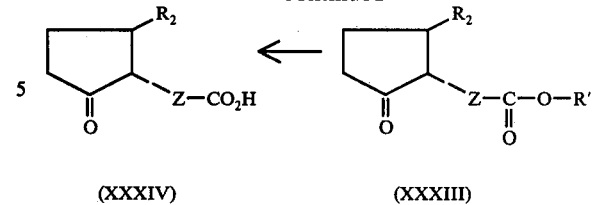

wherein R' is a lower alkyl group having up to 4 carbon atoms, R₂ is as hereinabove defined, and X is chloro, bromo or iodo. In general, Grignard reactions with conjugated ketones provide 1,2-addition products; conjugate 1,4-addition is usually accomplished when the reaction is carried out in the presence of a cuprous chloride or cuprous acetate catalyst. It is therefore most unexpected that the reaction of a cyclopentenone (XXXI) with a Grignard reagent (XXXII) in the presence of either of the aforementioned catalysts does not give appreciable amounts of the desired 1,4-conjugate addition product. The novel feature of our process is provided by the use, as a catalyst, of a cuprous halide complex with a trisubstituted phosphine, a trialkyl phosphonate, a tertiary amine or a heterocycle containing a basic nitrogen (e.g., pyridine). We have found it preferable to use tributylphosphine-cuprous iodide complex; $(C_4H_9)_3$ P.CuI. Thus, the preferred procedure for the preparation of the lower alkyl esters of the substituted 9-oxoprostanoic acids (XXXIII) involves the reaction of a cyclopentenone (XXXI) with a Grignard reagent (XXXII) in the presence of a trialkylphosphine-cuprous iodide complex (e.g., tributylphosphine-cuprous iodide). This reaction is best carried out in the usual way in an ether-type solvent such as diethyl ether, dibutyl ether, tetrahydrofuran, and the like, at room temperature for a period of time of from two to eighteen hours. The product (XXXIII) is then obtained by hydrolyzing the intermediate magnesium halide-enolate derivative, preferably with ammonium chloride, and isolating in the usual manner. In order to carry out this process, X in the Grignard reagent (XXXII) may be chlorine, bromine or iodine; but is preferably iodine.

Alternatively, conjugate 1,4-addition can also be effected by another process which involves treatment of a cyclopentenone (XXXI) with a lithio dialkyl cuprate (XXXVII) in accordance with the following reaction scheme:

FLOWSHEET F

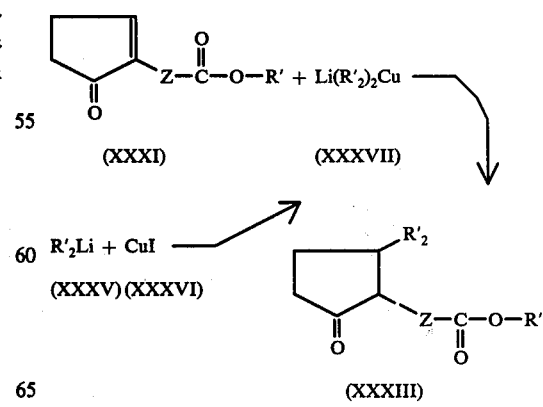

wherein R' and R'₂ are each a lower alkyl group having from one to four carbon atoms and Z is as hereinabove defined. The lithio dialkyl cuprate reagents (XXXVII) are prepared by treatment of a lower alkyl lithium (XXXV) with cuprous iodide (XXXVI), preferably at low temperatures (−5° C. to −20° C.) in an ether-type solvent. The reaction of (XXXI) with (XXXVII) is carried out in the usual way in an ether-type solvent at low temperatures (−5° C. to −20° C.) for a period of time of a few hours. The product (XXXIII) is obtained by quenching the reaction mixture with aqueous ammonium chloride solution and isolating in the usual manner.

The esters (XXXIII) may be hydrolyzed to the acids (XXXIV) by treatment with mild alkali, for example, 0.1N KOH in 50% methanol-water at ambient temperature for 15–20 hours. The acids (XXXIV) may be obtained directly by employing a 2-(ω-carboxyalkyl)cyclopent-2-en-1-one as starting material in lieu of the esters thereof (XXXI) but this is not preferred since an additional mole equivalent of Grignard reagent (XXXII) must be employed.

When the cyclopentanone esters (XXXIII) are formed by quenching of the reaction mixture with aqueous ammonium chloride solution, the relative stereochemical relationship of the two side-chains is not known with certainty. However, in any case, the subsequent hydrolysis of (XXXIII) to (XXXIV) ensures the development, at least in predominant proportion, of the thermodynamically favored trans-relationship between the two side-chains, as is depicted in structures (XXXIII) and XXXIV) of the reaction schemes of Flowsheets E and F. Alternatively, submission of the esters (XXXIII) to alkaline or acidic, but non-hydrolytic, conditions in an anhydrous alcoholic solvent will ensure formation of the favored trans-relationship.

Certain of the novel compounds of the present invention may be prepared by the catalytic hydrogenation of a substituted 9-oxo-13-trans-prostenoic acid, or lower alkyl ester thereof, as set forth in the following reaction scheme:

FLOWSHEET G

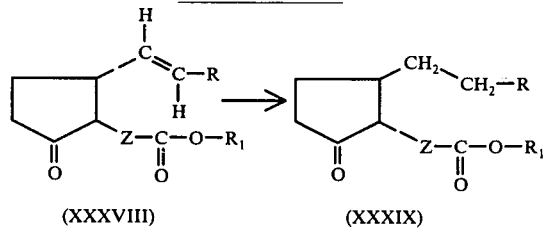

(XXXVIII)                (XXXIX)

This reduction is carried out with a noble metal catalyst in the usual manner for reducing double bonds. Reduction can also be accomplished with diimide as the reducing agent.

All of the compounds of this invention can be isolated and purified by conventional methods. Isolation can be accomplished, for example, by dilution of the reaction mixture with water, extraction with a water-immiscible solvent such as methoxylene chloride, ethyl acetate, benzene, cyclohexane, ether, toluene and the like, chromatography, adsorption on ion-exchange resins, distillation, or a combination of these. Purification of the compounds of this invention can be accomplished by means known in the art for the purification of prostaglandins and lipids, fatty acids, and fatty esters. For example, reverse phase partition chromatography, countercurrent distribution, adsorption chromatography on acid washed Florisil ® (synthetic magnesium silicate) and acid washed silica gel, preparative paper chromatography, preparative thin layer chromatography, chromatography over silver loaded cation exchange resins, and combinations thereof can be used effectively to purify the compounds produced by the processes of this invention.

The racemic products and intermediates of this invention can be resolved into their optically active components by a number of methods of resolution well known in the art. For example, acids can be treated with an optically active base such as cinchonine, quinine, brucine, d- or 1-α-phenyletylamine and the like to produce distereoisomeric salts which can be separated by crystallization. Alternatively, the acid may be esterified with an optically active alcohol, e.g., d- or 1-methanol, estradiol 3-acetate, etc., and the diastereoisomeric esters then resolved.

Resolution of the racemic prostaglandin-like compounds of this invention can also be accomplished by reverse phase and absorption chromatography on an optically active support and adsorbent and by selective transformation of one isomer with a biologically-active prostaglandin transforming system. Such transformations can be carried out by incubation or perfusion using methods well established in the art, followed by isolation and recovery of the isomer resistant to the metabolic transformation applied.

The novel substituted 9-oxoprostanoic acids and esters and salts thereof of the present invention are useful as antimicrobial agents and posses antibacterial and antifugal activity in vitro against a variety of standard laboratory microorganisms as determined by the agar-dilution streak-plate technique. In this assay, the compounds to be tested are made up to contain 2.5 mg. of test compound per milliliter of solution. Observing sterile techniques, two-fold serial dilutions are made of each test solution. One milliter of each of the original solutions and of each of the serial dilutions is then added to 9 ml. of warm sterile nutrient agar capable of supporting growth of the bacterial test cultures. A second set of agar dilutions is prepared identical to the first except that the nutrient agar is designed to support the growth of the fungal test cultures. The standard sterile nutrient agar solutions containing the different dilutions of the test compounds, along with suitable and comparable control dilutions containing no test compound, are then allowed to cool in Petri dishes thereby forming solidified agar plates. The test bacteria, and yeast-like fungi are prepared for use by growing in broth overnight. The spores of the filamentous fungi are harvested from mature agar slant cultures and are suspended in sterile physiological saline solution. A loopful of each of the resulting live suspensions is then, still employing sterile techniques, streaked upon the surfaces of each of the agar plates and the resulting streaked plates are then incubated. After an appropriate period of time, each of the streaks on each of the plates is inspected visually and the extent, if any, of bacterial or fungal growth is noted. The minimal inhibitory concentration (expressed in micrograms per millileter) is defined as the concentration of test compound causing complete inhibition of growth of any particular organism.

In a representative operation, and merely by way of illustration, the minimal inhibitory concentration of typical compounds of the present invention against a variety of test organisms as determined in the above-described assay are set forth in Table I below:

TABLE I

| Compound | Minimal inhibitory conc. (mcg/ml.) | | | |
|---|---|---|---|---|
| | (1) | (2) | (3) | (4) |
| 9-Oxoprostanoic acid | 25 | 100 | 50 | 50 |
| Ethyl 9-Oxo-17,18,19,20-tetranorprostanoate | 250 | 250 | 250 | 250 |
| Ethyl 9-Oxo-15,16,17,18,19,20-hexanorprostanoate | 62 | | 250 | 250 |
| Ethyl 9-Oxo-14,15,16,17,18,19,20-heptanorprostanoate | 62 | 100 | 50 | 50 |
| Ethyl 9-Oxo-3-Oxa-14,15,16,17,18,19,20-heptanorprostanoate | | | 250 | 250 |
| Ethyl 9-Oxo-10a-homo-14,15,16,17,18,19,20-heptanorprostanoate | 250 | | 50 | 50 |
| Ethyl 9-Oxo-18,19,20-trinorprostanoate | 62 | | 250 | |
| 9-Oxo-7a,7b-bishomo-14,15,16,17,18,19,20-heptanorprostanoic Acid | | | 250 | 250 |
| 9-Oxo-14,15,16,17,18,19,20-heptanorprostanoic Acid | | | 250 | 250 |

(1) *Mycobacterium amegmatin*, ATCC 606
(2) *Microsporum gypseum*, ATCC 14683
(3) *Trichophyton tonsurans*, NIH 662
(4) *Trichophyton mentagrophytes*, E 11

Topical preparations containing the 9-oxoprostanoic esters, acids or cationic salts thereof, it is expected, will provide particularly useful. Such compositions would be designed for administration to subjects exposed to, or infected with sensitive bacteria or fungi for either treatment or prophylaxis and may include ointments, creams, emulsions, unguents, salves, emollients, sprays, washes or the like. In addition, the compounds may be used in the form of solutions, suspensions, emulsions, washes, powders, dusts, mists, soaps, sprays, aerosols, drenches, or other forms for the purpose of cleaning, disinfecting, or sterilizing surgical instruments, laboratory glassware or instruments, hospital walls or other surface, linens, dishes, laboratory tables, coops, cages, or the like. Likewise these compounds might be incorporated into soaps, detergents, sprays or the like in the home, farm, office or elsewhere with the purpose of preventing or minimizing infection or contamination with sensitive bacteria or fungi. Painting, spraying, immersion or other means of effecting contact may be applied. The ester derivatives of this invention are also useful as intermediates for the preparation of the corresponding carboxylic acids and salts thereof.

9-Oxoprostanoic acid is also a valuable central nervous system depressant of low toxicity and was shown to possess CNS depressant activity as determined by animal experiments as follows. The compound was administered intraperitoneally in a 2 starch vehicle to groups of six mice at three or more graded dose levels. At 15-minute and 30-minute intervals after treatment, each animal was placed on the midpoint of a horizontal steel rod (1.55 cm. in diameter and about 6 dm. in length), positioned 45.7 cm. above the surface of the table, and forced to walk toward a platform at either end of the rod. The criterion of inability to perform this act was consistent slipping to the side or falling off the rod. Effective dose for reduced rod-walking ability ($RWD_{50}$) were calculated or approximated from the data, and the time of peak effect was estimated from the data. One-half of the $RWD_{50}$ dose was given intraperitoneally to each mouse in groups of five. At the time of peak effect, as determined above, each group of mice was put into the acetophotometer for a period of five minutes and the motor activity counts were recorded and compared to controls. Since the compound appeared to reduce motor activity by 50%, it was administered to additional groups of five mice at graded doses and tested similarly. The dose ($MDD_{50}$) that caused a 50% reduction in motor activity was estimated. In a representative operation, 9-oxoprostanoic acid was shown to reduce locomotor activity ($MDD_{50}$) at a dose of 19 mg./kg. of body weight (IP), This compound also shows anticonvulsant activity, protecting 40% of strychnine-treated mice at a dose of 50 mg./kg. of body weight (IP).

The novel compounds of the present invention are useful as hypotensive agents and their prostaglandin-like hypotensive activity was demonstrated in the following test procedure. This procedure is a modification of the technique described by Pike et al., *Prostaglandins, Nobel Symposium* 2, Stockholm, June 1966; page 165, Interscience Publishers (New York, 1967).

Male Wistar strain rats (Royal Hart Farms) averaging approximately 250 grams in weight were fastened to rat boards in a supine position by means of canvas vests and limb ties. The femoral area was infiltrated subcutaneously with lidocaine and the iliac artery and vein were exposed and cannulated. Arterial blood pressure (systolic/diastolic) was recorded using a Statham $P_{23}$ Db pressure transducer-Offner dynograph system. To obtain a stable blood pressure, the animals were anesthetized before use with pentobarbital, 30 mg./kg. of body weight intravenously, and also were given hexamethonium bitartrate, 2 ,mg./kg. of body weight intravenously. The test compounds were prepared by ultrasonic dispersion in a saline-Tween 80 ® vehicle. A constant intravenous dose volume of 0.5 ml. was administered and test doses ranged from 0.1 to 10.0 mg./kg. of body weight. Increasing or decreasing doses were selected depending on the dose response obtained In Table II below are set forth the minimal doses required to produce a decrease of about 10 mm. in diastolic blood pressure for typical compounds of the present invention.

TABLE II

| Compound | Effective Dose (mg./kg. of body weight) |
|---|---|
| 9-Oxoprostanoic Acid | 2 |
| Ethyl 9-Oxoprostanoate | 2 |
| Ethyl 9-Oxo-17,18,19,20-tetranorprostanoate | 8 |
| 9-Oxo-7a,7b-bishomo-14,15,16,17,18,19,20-heptanorprostanoic acid | 2–8 |
| Ethyl 9-Oxo-10a-homo-14,15,16,17,18,19,20-heptanorprostanoate | 8 |
| Ethyl 9-Oxo-15,16,17,18,19,20-hexanorprostanoate | 0.2–2 |
| 9-Oxo-14,15,16,17,18,19,20-heptanorprostanoic acid | 2 |
| Ethyl 9-Oxo-14,15,16,17,18,19,20-heptanorprostanoate | 8 |

This hypotensive effect is short acting and a continuous infusion of compound is necessary to maintain the effect. Nevertheless, it is authoritatively claimed that hypotension induced by prostaglandins is of an ideal nature and therefore, despite the necessity of infusion, these compounds may be useful in the treatment of certain hypertensive crisis situations such as eclampsia. A description of this problem appears in the Medical Letter of Drugs and Therapeutics (p. 31–32, issue of Apr. 3, 1970). Also, in a news item from *Medical World News*, 10, 12 (August 1, 1969), Dr. J. B. Lee, associate professor of medicine at St. Louis University, is quoted as saying that the related prostaglandin A compounds "might be useful in a hypertensive crisis such as eclampsia." The natural prostaglandins are only difficulty available, and at great cost. Thus, although the prostaglandin congeners of this invention may be less potent and larger doses would probably be necessary, the greater availability of these congeners, when prepared by the methods of this invention, should provide a substantial economic advantage.

The novel compounds of the present invention are also effective inhibitors of gastric acid secretion and of ulcer development in experimental animals, and thus are potentially valuable as agents for the control of gastric acid secretion and of gastric erosion and as anti-ulcer agents. Gastric acid secretion inhibitory action is usually measured by the "Shay rat" procedure[1,2] with some modifications as follows.

[1]Shay et al., Gastroenterology 5, 43 (1945).
[2]Shay et al., Gastroenterology 26, 906 (1954).

The rats (male, CFE strain) were starved for 48 hours (water was given ad libitum) to permit evacuation of stomach contents. On the morning of the experiment, under ether anesthesia, the abdominal region was shaved and a midline incision (1–1½ inches) was made with a scapel. With the help of a closed curved hemostate the duodenum was picked up. Upon getting the duodenum into view, fingers were used to pull the stomach through the opening, the stomach was then gently manipulated with fingers to rid stomach of air and residual matter which were pushed through the pylorus. Two-5 inch sutures were drawn under the pyloric-duodenal puncture. A ligature, at the juncture, was formed with one of the threads. The second ligature was also formed but not tightened.

The test compound of the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Ocasionally, instead of an intraduodenal injection, animals were dosed by the oral or subcutaneous route. In the latter case, dosing was done thirty to sixty minutes before the operation.)

Three hours later, the rats were decapitated and exanguinated, taking care that blood did not drain into the esophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. H$_2$O were used to wash the stomach contents into the respective centrifuge tube. The combined stomach contents and wash were then centrifuged out for 10 min. in the International Size 2 Centrifuge (setting at 30). The supernatant was collected, volume measured and recorded, 2 drops of a phenylphthalein indicator (1% in 95% ethanol) were added and the solution was titrated with 0.02N NaOH (or with 0.04N NaOH when large volumes of stomach contents were encountered) to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with typical compounds of the present invention are given in Table III below.

TABLE III

| Compound | Intraduodenal Dose; mg./kg. of body weight | Percent Inhibition |
|---|---|---|
| 9-Oxo-14,15,16,17,18,19,20-heptanorprostanoic acid | 100 | 84 |
|  | 50 | 53 |
|  | 25 | 37 |
| Ethyl 9-Oxo-14,15,16,17,18,19,20-heptanorprostanoate | 100 | 93 |
|  | 50 | 58 |
|  | 100 (oral dose) | 78 |
| Ethyl 9-Oxo-15,16,17,18,19,20-hexanorprostanoate | 100 | 81 |
| Ethyl 9-Oxo-16,17,18,19,20-pentanorprostanoate | 100 | 54 |
| Ethyl 9-Oxo-17,18,19,20-tetranorprostanoate | 100 | 66 |
| Ethyl 9-Oxo-18,19,20-trinorprostanoate | 100 | 41 |
| Ethyl 9-Oxo-6,7,14,15,16,17,18,19,20-nonanorprostanoate | 100 | 88 |
| Ethyl 9-Oxo-10a-homo-14,15,16,17,18,19,20-heptanorprostanoate | 100 | 60 |
| Ethyl 9-Oxo-7a,7b-bishomo-14,15,16,17,18,19,20-heptanorprostanoate | 50 | 73 |
| 9-Oxo-7a,7b-bishomo-14,15,16,17,18,19,20-heptanorprostanoic acid | 100 | 91 |
| 9-Oxo-6,7,14,15,16,17,18,19,20-nonanorprostanoic acid | 50 | 86 |
| Ethyl 9-Oxo-3oxa-14,15,16,17,18,19,20-heptanorprostanoate | 200 | 55 |

The compounds of this invention also provide protection against the ulcerogenic properties of indomethacin. This assay was carried out in the following manner.

Rats were starved for 48 hours (water was given ad libitum). Indomethacin (20 mg./kg. of body weight) was administered by the subutaneous route and one-half the dose of the test compound was administered by gavage at the same time. After three hours, the second half of the test compound was administered, also by gavage. Five hours after the administration of indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported. [Abdel-Galil et al. Brit. J. Pharmac. Chemotherapy 33:1–14 (1968)].

| Score | |
|---|---|
| 0 | - Normal stomach |
| 1 | - Petechial hemorrhage or pin point ulcers |
| 2 | - 1 or 2 small ulcers |
| 3 | - Many ulcers, a few large |
| 4 | - Many ulcers, mainly large |

Control animals treated with indomethacin but not test compound consistently give scores of about 3.5–3.7. Control animals treated with neither indomethacin nor test compound give scores of about 0.5–0.8. The results obtained in this assay with typical compounds of the present invention are set forth in Table IV below. Compounds producing a score of 2.8 or lower are considered to be active.

TABLE IV

| Compounds | Total Oral Dose; mg./kg. of body weight | Score |
| --- | --- | --- |
| 9-Oxo-14,15,16,17,18,19,20-hepta-norprostanoic acid | 25 | 1.8 |
| Ethyl 9-Oxo-14,15,16,17,18,19,20-heptanorprostanoate | 100 | 1.2 |
| 9-Oxo-7a,7b-bishomo-14,15,16,17,18,19,20-heptanorprostanoic acid | 25 | 2.0 |

This invention will be described in greater detail in conjunction with the following specific examples.

EXAMPLE 1

Preparation of 2-carbalkoxy(methyl/ethyl)-2-(4-carbethosybutyl)cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°-143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately ½ hour. The solution is cooled and diluted with water and extracted with ether. The combined extracts are washed with saline and dried over magnesium sulfate and evaporated. The residue is evaporated twice with toluene to give 144 g. of an oil.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°-109° C. (0.23 mm).

EXAMPLE 4

Preparation of 2-carbalkoxy(methyl/ethyl)-2-(3-carbethoxypropyl)cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°-137° C. (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(3-carbethoxypropyl)cyclopentan-1-one

In the manner described in Example 3, treatment of 2-(3-carboxypropyl)cyclopentan-1-one (Example 5) with p-toluenesulfonic acid monohydrate in ethanol gives a colorless oil, b.p. 93° C. (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of ethyl (methyl) 7-(2-carbethoxycyclohexan-1-on-2-yl)heptanoate

To a stirred suspension of 51 g. of sodium hydride (57% in mineral oil) in 675 ml. of dimethylformamide is added 200 g. of 2-cyclohexanone carboxylate (60% ethyl – 40% methyl esters) over a 1-5 hr. period with external cooling to maintain the temperature at 20°-25° C. The reaction mixture is stirred at ambient temperature for 15 minutes and heated to 50° C. over 15 minutes. To the stirred mixture is added 300 g. of ethyl 7-bromoheptanoate during a 10 minute period. The reaction mixture is stirred at 50°-60° C. for 4 hours, cooled, and poured into water. The product is obtained by ether extraction. The extract is washed successively with water and saturated sodium chloride, dried and evaporated to give a liquid which is purified by distillation, IR 1735 cm$^{-1}$ (ester carbonyls) and 1710 cm$^{-1}$ (ketone carbonyl).

EXAMPLE 11

Preparation of 7-(cyclohexan-1-on-2-yl)heptanoic acid

A stirred mixture of 380 g. of mixed methyl and ethyl esters of 7-(2-carbethoxycyclohexan-1-on-2-yl)heptanoate (Example 10), 202 ml. of concentrated sulfuric acid, 970 ml. of glacial acetic acid, and 970 ml. of water is refluxed for 22.5 hours. The cooled reaction mixture is treated with 380 g. of sodium carbonate and 2 liters of water and is extracted with ether. Acidic material is partitioned from the ether extract with 1.0M sodium carbonate. The aqueous phase is acidified with concentrated hydrochloric acid and extracted with ether. The extract is washed successively with water and saturated sodium chloride, dried, and evaporated to give an oil.

EXAMPLE 12

Preparation of ethyl 7-(cyclohexan-1-on-2-yl)heptanoate

A solution of 232 g. of 7-(cyclohexan-1-on-2)heptanoic acid in 2500 ml. of ethanol is refluxed for 4.5 hours with 3.8 g. of p-toluenesulfonic acid monohydrate. The solution is diluted with 200 ml. of benzene, and boiling is continued for 2 hours as 200 ml. of distillate is removed. The volume of the solution is concentrated to 500 ml. After dilution with 500 ml. of ether the solution is extracted with a solution prepared from 50 ml. of saturated sodium bicarbonate, 50 ml. of saturated sodium chloride, and 100 ml. of water. The extract is washed with saturated sodium chloride, dried, and evaporated. The product is purified by distillation to give a liquid, IR 1740 cm$^{-1}$ (ester carbonyl) and 1715 cm$^{-1}$ (ketone carbonyl).

EXAMPLE 13

Preparation of 1-acetoxy-2-(6-carbethoxyhexyl)cyclopent-1-ene

A stirred solution of 100 g. of 2-(6-carbethoxyhexyl)-cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreaux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 14

Preparation of 1-acetoxy-2-(3-carbethoxypropyl)cyclopent-1-ene

In the manner described in Example 13, treatment of 2-(3-carbethoxypropyl)cyclopentan-1-one (Example 6) with acetic anhydride and p-toluenesulfonic acid monohydrate gives a yellow oil, b.p. 98°-103° C. (0.35 mm).

EXAMPLE 15

Preparation of 1-acetoxy-2-(4-carbethoxybutyl)cyclopent-1-ene

In the manner described in Example 13, treatment of 2-(4-carbethoxybutyl)cyclopent-1-one (Example 3) with acetic anhydride and p-toluenesulfonic acid monohydrate gives a yellow oil, b.p. 109°-110° C. (0.37mm).

EXAMPLE 16

Preparation of ethyl 7-(1-acetoxycyclohex-1-en-2-yl)heptanoate

A stirred solution of 28.0 g. of ethyl 7-(cyclohexan-1-on-2-yl)heptanoate (Example 12), 170 mg. of p-toluenesulfonic acid monohydrate, and 25.6 g. of acetic anhydride is heated for 5 hours while allowing 8.0 g. of distillate to distill. The cooled solution is poured into a stirred, ice-cold mixture of 500 ml. of saturated sodium bicarbonate and 250 ml. of hexane. After one hour the hexane phase is separated, dried, and evaporated. The crude product is distilled to give a liquid, IR 1760 cm$^{-1}$ (vinyl ester carbonyl) and 1740 cm$^{-1}$ (ethyl ester carbonyl).

EXAMPLE 17

Preparation of 2-(6-carbethoxyhexyl)cyclopent-2-1-one

To a rapidly stirred mixture of 50 g. of 1-acetoxy-2-(6-carbethoxyhexyl)cyclopent-1-ene (Example 13) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times. The combined ether extracts are washed with saturated sodium chloride solution, dried with anhydrous magnesium sulfate and taken to dryness under reduced pressure to afford 41.5 g. of the amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is disssolved in ether and washed with saturated sodium bicarbonate solution, saturated sodium chloride solution, dried with anhydrous magnesium sulfate and taken to dryness under reduced pressure. The residual oil is distilled to give 30.2 g. of product; b.p. 118° C. (0.05 mm); $\lambda H_{max}$MeOH 229 $\mu$ ($\epsilon$9950): $\lambda_{max}$ 5.75, 5,85, 6.15, 8.45 $\mu$; vapor phase chromatography shows 99% product, containing 1% 2-(6-carbethoxyhexyl)cyclopentan-1-one.

This product can be purified by the following procedure. A mixture of 120 g. of 2-(6-carbethoxyhexyl)-2-cyclopentenone, containing approximately 5% of the saturated analogue, and 7.67 g. (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing <0.5% of the saturated impurity.

EXAMPLE 18

Preparation of 2-(3-carbethoxypropyl)cyclopent-2-en-1-one

In the manner described in Example 17, bromination of 1-acetoxy-2-(3-carbethoxypropyl)cyclopent-1-ene (Example 14) followed by dehydrobromination with lithium bromide and lithium carbonate is productive of the subject compound.

EXAMPLE 19

Preparation of 2-(4-carbethoxybutyl)cyclopent-2-en-1-one

In the manner described in Example 17, treatment of 1-acetoxy-2-(4-carbethoxybutyl)cyclopent-1-ene (Example 15) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 17 furnishes a product which contains less than 0.5% of the corresponding saturated ketone.

EXAMPLE 20

Preparation of 1-methoximino-2-(6-carbethoxyhexyl)-2-cyclopentene

To a mixture of 35.97 g. (0.151 mole) of 2-(6-carbethoxyhexyl)-2-cyclopentenone (Example 17) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried ($Na_2SO_4$), and the solvent is evaporated to yield an oil. Distillation yields 38.7 g. of a colorless oil, b.p. 115°–118° C. (0.075 mm). IR (film): 1740, 1627, 1053, 890 $cm^{-1}$. $\lambda_{max}$ (MeOH) 243 (13,000). NMR$\delta$($CDCl_3$): 3.89.

EXAMPLE 21

Preparation of 1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 20) in 200 ml. of benzene under nitrogen is added dropwise 225 ml. of a 25% solution of diisobutyl aluminum hydride in hexane. The resulting solution is stirred for 2 hours at 0°–5° C., poured onto ice and dilute hydrochloric acid, and the aqueous phase is saturated with sodium chloride. The organic phase is separated, washed with saturated brine, dried ($Na_2SO_4$), and evaporated to yield an oil. The latter is dissolved in 100 ml. of hot hexane and cooled to yield 24.3 g. of crystals, m.p. 62°–64° C. IR (KBr) 3260, 1630, 1059, 893 $cm^{-1}$. $\lambda_{max}$243 (14,200). NMR ($CDCl_3$)$\delta$: 2.37.

EXAMPLE 22

Preparation of 1-methoximino-2-(7-p-toluenesulfonyloxyheptyl)-2-cyclopentene

To a solution of 5.00 g. (0.0222 mole) of 1-methoximino-2-(7-hydroxyheptyl)-2-cyclopentene (Example 21) in 50 ml. of dry pyridine at 0° C. is added 8.45 g. (0.0444 mole) of p-toluenesulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried ($NaSO_4/K_2CO_3$), and evaporated under reduced pressure at room temperature to yield an oil. The latter is dissolved in 600 ml. of hexane, treated with 0.5 g. of Darco, filtered and evaporated to yield 7.7 g. of a colorless oil. IR (film) 1600, 1192, 1182, 1053, 890 $cm^{-1}$. $\lambda_{max}$ (MeOH) 228 and 243.

EXAMPLE 23

Preparation of 1-methoximino-2-(8,8-dicarbethoxyoctyl)-2-cyclopentene

To an alcoholic solution of sodiodiethyl malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 22 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 $cm^{-1}$.

EXAMPLE 24

Preparation of 1-methoximino-2-(8,8-dicarboxyoctyl)-2-cyclopentene

A mixture of 6.45 g. of the diester of Example 23 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°–137° C. (—$CO_2$).

EXAMPLE 25

Preparation of 1-methoximino-2-(8-carboxyoctyl)-2-cyclopentene

A solution of 3.926 g. (0.0126 mole) of the diacid of Example 24 in 20 ml. of xylene is refluxed for 1.5 hours, cooled, and evaporated to yield a tan solid. IR (KBr) 1720, 1618, 1179, 1050, 986 $cm^{-1}$.

EXAMPLE 26

Preparation of 2-(8-carboxyoctyl)cycopent-2-en-1-one

The acid methoxime from Example 25 is refluxed for 5 hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried (Na$_2$SO$_4$), and evaporated to yield a tan solid. IR (KBr) 1745, 1665 cm$^{-1}$. $\lambda_{max}$ (MeOH) 228 (12,600).

EXAMPLE 27

Preparation of 2-(8-carbethoxyoctyl)cyclopent-2-en-1-one

The acid ketone from Example 26 is Fisher esterified with 100 ml. of absolute ethanol, 100 ml. of benzene, and 20 mg. of p-toluenesulfonic acid for 6 hours, cooled, and the solvent is evaporated. The resulting oil is dissolved in 3:1 benzene-ether and the solution is passed through a column of 100 g. of Florisil ®. The filtrate is evaporated and the residue is distilled to yield 2.97 g. of a colorless oil, b.p. 137°–139° C. (0.05 Torr).

EXAMPLE 28

Preparation of ethyl 7-(cyclohex-2-en-1-one-2-yl)heptanoate

To a stirred solution of ethyl 7-(1-acetoxycyclohex-1-en-2-yl)heptanoate (Example 16) in 750 ml. of acetic acid and 125 ml. of pyridine at 10° C. is added a solution of 13.8 g. of bromine in 200 ml. of acetic acid over 20 minutes. The resulting solution is allowed to stand at ambient temperature for 45 minutes and is then decolorized with sodium sulfite. The solution is poured into 800 ml. of half-saturated sodium chloride and extracted with 1:1 hexane-ether. The extract is washed successively with water and saturated sodium chloride, dried over sodium carbonate, and evaporated to give 32 g. of the crude bromoketone. To a stirred suspension of 14.2 g. of lithium bromide and 16.6 g. of lithium carbonate in 250 ml. of anhydrous dimethylformamide at 80° C. is added the above bromoketone. The stirred mixture is heated to boiling over 20 minutes and refluxed for 15 minutes. The cooled mixture is poured into 1000 ml. of water, acidified with dilute hydrochloric acid, and extracted with ether. The extract is washed successively with water and saturated sodium chloride, dried, and evaporated. The product is purified by distillation to give a liquid, IR 1740 cm$^{-1}$ (ester carbonyl), 1685 cm$^{-1}$ (ketone carbonyl), and 1650 cm$^{-1}$ (olefin); NMR (CCl$_4$) 6.63 (multiplet, vinyl proton).

EXAMPLE 29

Preparation of ethyl 9-oxo-13-trans-prostenoate

A solution of 1.102 g. of 1-octyne in 2 ml. of benzene is treated with 11.5 ml. of 15% diisobutylaluminum hydride in toluene and the solution is heated to 50° C. for 2 hours. The solution is cooled, its solvent is removed in vacuo, and the resulting oil is treated with 5.45 ml. of 5.10% methyl lithium in diethyl ether with ice cooling. To the resulting solution is added 1.830 g. of 2-(6-carbethoxyhexyl)-2-cyclopentenone (Example 17) and the solution is stirred at ambient temperatures for 18 hours. The solution is poured onto ice and dilute hydrochloric acid, and the mixture is extracted with diethyl ether. The organic phase is washed with dilute sodium bicarbonate, water, and saturated brine, dried, and evaporated. The residue is purified by chromatography on Florisil ® and distillation to yield 1.878 g. of an oil, IR 1736 cm$^{-1}$ (ester and ketone carbonyls 969 cm$^{-1}$ (trans vinyl group); NMR (CDCl$_3$)δ5.14–5.87 (multiplet, 2H, vinyl protons, J trans=15 Hz); Mass Spectrum, parent peak at 350 mu.

EXAMPLE 30

Preparation of ethyl 9-oxo-18,19,20-trinor-13-trans-prostenoate

In the manner described in Example 29, 2-(6-carbethoxyhexyl)-2-cyclopentenone (Example 17) is added to the reagent prepared from 1-pentyne, diisobutylaluminum hydride, and methyl lithium. The crude product obtained by acid hydrolysis and ether extraction is purified by distillation to give a liquid, IR 1740 cm$^{-1}$ (ester and ketone carbonyls) 967 cm$^{-1}$ (trans vinyl group).

EXAMPLE 31

Preparation of ethyl 9-oxo-20-nor-13-trans-prostenoate

A solution of 5.30 g. of 1-heptyne in 10 ml. of benzene is treated with 40 ml. of 1.2N diisobutylaluminum hydride in hexane and heated at 50° C. for 2 hours. The solution is cooled in an ice bath and diluted with 25 ml. of ether. To the solution is added 30 ml. of 1.6M n-butyl lithium in hexane. After stirring for 20 minutes at 15°–25° C. the resulting solution is treated with a solution of 2-(6-carbethoxyhexyl)-2-cyclopentenone (Example 17). The mixture is stirred at 5°–25° C. for 18–20 hours and the product then is hydrolyzed with a mixture of ice and hydrochloric acid. The crude product, obtained from the organic phase, is purified by chromatography on silica gel to give an oil, IR 1740 cm$^{-1}$ (ester and ketone carbonyls) and 967 cm$^{-1}$ (trans vinyl group).

EXAMPLE 32

Preparation of ethyl 20-methyl-9-oxo-13-trans-prostenoate

In the manner described in Example 31, 2-(6-carbethoxyhexyl)-2-cyclopentenone (Example 17) is added to the reagent prepared from 1-nonyne, diisobutylaluminum hydride and n-butyl lithium. The crude product obtained by acid hydrolysis and evaporation of organic solvent is purified by chromatography on silica gel to give an oil, IR 1740 cm$^{-1}$ (ester and ketone carbonyls) and 967 cm$^{-1}$ (trans vinyl group).

EXAMPLE 33

Preparation of ethyl 9-oxo-6,7-dinor-13-trans-prostenoate

In the manner described in Example 29, 2-(4-carbethoxybutyl)-2-cyclopentenone (Example 19) is added to the reagent prepared from 1-octyne, diisobutylaluminum hydride, and methyl lithium. The product is obtained by acid hydrolysis, ether extraction and distillation to yield a colorless oil, b.p. 149°–150° C. (0.075 mm.). IR 1740 cm$^{-1}$ (ester and ketone carbonyls) 963 cm$^{-1}$ (trans-vinyl group).

EXAMPLE 34

Preparation of ethyl 9-oxo-7a,7b-bis-homo-13-trans-prostenoate

In the manner described in Example 29, 2-(8-carbethoxyoctyl)-2-cyclopentenone (Example 27) is added to the reagent prepared from 1-octyne, diisobutylaluminum hydride, and methyl lithium. The crude product obtained by acid hydrolysis and ether extraction is purified by silica gel chromatography to give an oil, IR 1740 cm$^{-1}$ (ester and ketone carbonyls), 967 cm$^{-1}$ (trans-vinyl group).

EXAMPLE 35

Preparation of 2-(4-carbethoxybutyl)-2-cyclopentenonemethoxime

Treatment of 2-(4-carbethoxybutyl)-2-cyclopentenone (Example 19) with methoxyamine hydrochloride in the manner described in Example 20 gives an oil, b.p. 107°–109° C. (0.05 mm). IR (film): 1740, 1628, 1050, 885 cm$^{-1}$. $\lambda_{max}$ (MeOH) 243 (13,600).

EXAMPLE 36

Preparation of 2-(5-hydroxypentyl)-2-cyclopentenomethoxime

Treatment of 2-(4-carbethoxybutyl)-2-cyclopentenomethoxime (Example 35) with diisobutyl aluminum hydride in the manner described in Example 21 gives crystals, m.p. 33°–35° C. IR (KBr) 3420, 1630, 1050, 886 cm$^{-1}$. $\lambda_{max}$ MeOH 243 (12,020).

EXAMPLE 37

Preparation of 2-(5-tosylpentyl)-2-cyclopentenomethoxime

Treatment of 2-(5-hydroxypentyl)-2-cyclopentenomethoxime (Example 36) with p-toluenesulfonyl chloride in pyridine in the manner described in Example 22 gives a colorless oil. IR (film) 1600, 1190, 1180, 1050, 885 cm$^{-1}$.

EXAMPLE 38

Preparation of 2-(6,6-dicarbethoxyoctyl)-2-cyclopentenomethoxime

To a solution of sodio diethyl ethymalonate, prepared from 1.63 g. (0.0387 mole) of sodium hydride in mineral oil (57.2%), 100 ml. of ethylene glycol dimethyl ether and 8.5 g. (0.0452 mole) of ethyl diethyl malonate, is added 7.5 g. of tosylate from Example 37 in 20 ml. of ethylene glycol dimethyl ether and the mixture is refluxed for 3 hours and then allowed to stand at room temperature for 18 hours under nitrogen atmosphere. The reaction mixture is filtered and most of the solvent is removed. The mixture is partitioned between cold dilute hydrochloric acid and diethyl ether, and the organic phase is washed with water and saturated brine, dried (MgSO$_4$), and evaporated to yield an oil. The excess ethyl diethyl malonate is distilled off under reduced pressure to yield 6.7 g. of a yellow oil. IR (film) 1755, 1728, 1627, 1050, 885 cm$^{-1}$.

EXAMPLE 39

Preparation of 2-(6,6-dicarboxyoctyl)-2-cyclopentenomethoxime

Treatment of 2-(6,6-dicarbethoxyoctyl)-2-cyclopentenomethoxime (Example 38) with potassium hydroxide, and 1:1 aqueous methanol in the manner described in Example 24 gives a light yellow oil.

EXAMPLE 40

Preparation of 2-(6-carboxyoctyl)-2-cyclopentenomethoxime

In the manner described in Example 25, treatment of 2-(6,6-dicarboxyoctyl)-2-cyclopentenomethoxime (Example 39) with xylene at reflux for 18 hours gives a yellow oil.

EXAMPLE 41

Preparation of 2-(6-carboxyoctyl)-2-cyclopentenone

Treatment of 2-(6-carboxyoctyl)-2-cyclopentenomethoxime (Example 40) with acetone and 2N hydrochloric acid in the manner described in Example 26 gives a light yellow oil.

EXAMPLE 42

Preparation of 2-(6-carbethoxyoctyl)-2-cyclopentenone

Treatment of 2-(6-carboxyoctyl)-2-cyclopentenone (Example 41) with thionyl chloride and then treatment of the acid chloride with ethanol in the usual manner gives an amber oil. The oil is placed on a magnesia-silica gel column and eluted with 3:1 benzene:ether. The solvent is removed and the residue is distilled, b.p. 122° C. (0.06 mm).

EXAMPLE 43

Preparation of diethyl 1,1-dimethyl-5-tetrahydropyranylpentylmalonate

To 486 mg. (0.02 g.-atoms) of magnesium in 5 ml. of toluene containing one molar equivalent of tetrahydrofuran per equivalent of magnesium and one percent iodine (calculated in weight of magnesium) is added dropwise 3.86 g. (0.02 mole) of 4-chloro-1-tetrahydropyranyloxybutane over a period of one hour with stirring, under nitrogen at 70° C. The reaction mixture is stirred at 70° C. for four hours. This reagent is then added dropwise to 3 g. (0.015 mole) of ethyl isopropylidenemalonate in 40 ml. of tetrahydrofuran containing 392 mg. of tetrakis [iodo(tri-n-butylphosphine)-copper (I)] and stirred at room temperature for 2 hours. The reaction mixture is poured into cold dilute hydrochloric acid and extracted with ether. The ether extract is dried over magnesium sulfate and concentrated to give 5.92 g. of subject product as an oil.

EXAMPLE 44

Preparation of diethyl 1,1-dimethyl-5-hydroxypentylmalonate

A solution of 3.5 g. (0.01 mole) of diethyl 1,1-dimethyl-5-tetrahydrofuranyloxypentylmalonate in 70 ml. of ethanol containing 3 ml. of hydrochloric acid is allowed to stir at room temperature for 18 hours. The solution is concentrated, diluted with water and extracted with ether. The ether extract is washed with water, dried over magnesium sulfate and concentrated to give 3.262 g. of a light yellow oil. The oil is purified by distillation, b.p. 116°–117° C. (0.05 mm).

EXAMPLE 45

Preparation of 3,3-dimethyl-7-hydroxyheptanoic acid

A mixture of 32 g. (0.117 mole) of diethyl 1,1-dimethyl-5-hydroxypentylmalonate, 25 g. of potassium hydroxide and 600 ml. of methanol-water (1:1) is heated at reflux for 8 hours and then allowed to stand at room temperature for 18 hours. The methanol is removed, diluted with water and the reaction mixture is acidified with concentrated hydrochloric acid. The mixture is extracted with ether. The extract is washed with water and saline, dried over anhydrous magnesium sulfate and concentrated to give 27 g. of 1,1-dimethyl-5-hydroxypentylmalonic acid. This crude oil is dissolved in 200 ml. of bis-(2-methoxyethyl)ether and is heated at reflux for 4 hours and then allowed to stand at room temperature overnight. The solution is removed and the reaction mixture is diluted with water and extracted with ether. The organic solution is washed with saline, dried over magnesium sulfate and concentrated to give 18 g. of product as an oil.

EXAMPLE 46

Preparation of ethyl 3,3-dimethyl-7-chloroheptanoate

To a solution of 3.484 g. (0.02 mole) of 3,3-dimethyl-7-hydroxyheptanoic acid in 25 ml. of chloroform containing 3 drops of dimethylformamide is added 5.8 ml. (0.08 mole) of thionyl chloride and the solution is then heated at reflux for 3–4 hours. The solution is concentrated to give the intermediate 3,3-dimethyl-7-chloro-1-heptanoyl chloride. The acid chloride is dissolved in a minimum amount of benzene and added slowly to 20 ml. benzene, 10 ml. of ethanol and 2.65 ml. of collidine. The solution is heated at reflux for one hour and then concentrated. The residue is dissolved in ether, washed with water, dilute sodium bicarbonate solution and saline. The organic solution is dried over magnesium sulfate and concentrated to give 3.57 g. of product as a yellow oil.

EXAMPLE 47

Preparation of ethyl 3,3-dimethyl-7-iodoheptanoate

To a solution of 3.57 g. (0.0162 mole) of ethyl 3,3-dimethyl-7-chloroheptanoate in 100 ml. of methyl ethyl ketone is added 4 g. of sodium iodide and the mixture heated at reflux for 18 hours. The reaction mixture is cooled, filtered and concentrated. The residue is partitioned between ether and water. The aqueous phase is extracted several times with ether. The extract is washed with sodium bisulfite solution, water and saline. The organic solution is dried over magnesium sulfate and concentrated to give 4.182 g. of a yellow oil. The material is purified by distillation, b.p. 86°–87° C. (0.18 Torr).

EXAMPLE 48

Preparation of 2-carbalkoxy(methyl/ethyl)-2-(6-carbethoxy-5,5-dimethylhexyl)cyclopentan-1-one This compound is prepared by treatment of sodio cyclopentanone carboxylate enolate with ethyl 3,3-dimethyl-7-iodoheptanoate by the procedure described in Example 1.

EXAMPLE 49

Preparation of 2-(6-carboxy-5,5-dimethylhexyl)cyclopentan-1-one

This compound is prepared by decarbalkoxylation of 2-carbalkoxy (mixed methyl and ethyl ester)-2-(6-carbethoxy-5,5-dimethylhexyl)cyclopentan-1-one by the procedure described in Example 2.

EXAMPLE 50

Preparation of 2-(6-carbethoxy-5,5-dimethylhexyl)cyclopentan-1-one

Esterification of 2-(6-carboxy-5,5-dimethylhexyl)cyclopentan-1-one with ethanol is productive of the subject compound.

EXAMPLE 51

Preparation of 1-acetoxy-2-(6-carbethoxy-5,5-dimethylhexyl)cyclopent-1-ene

This compound is prepared from 2-(6-carbethoxy-5,5-dimethylhexyl)cyclopentan-1-one and acetic anhydride by the process described in Example 13.

EXAMPLE 52

Preparation of 2-(6-carbethoxy-5,5-dimethylhexyl)cyclopent-2-en-1-one

This compound is prepared from 1-acetoxy-2-(6-carbethoxy-5,5-dimethylhexyl)cyclopent-1-ene via bromination and dehydrobromination according to the procedure described in Example 17.

EXAMPLE 53

Preparation of 2-(3-carbethoxypropyl)-1-methoxyimino-2-cyclopentene

In the manner described for the preparation of the compound of Example 20, 2-(3-carbethoxypropyl)-1-methoximino-2-cyclopentene is prepared from 2-(3-carbethoxypropyl)-2-cyclopentenone (Example 18) and methoxyamine hydrochloride.

EXAMPLE 54

Preparation of 2-(4-hydroxybutyl)-1-methoximino-2-cyclopentene

In the manner described for the preparation of the compound of Example 21, 2-(4-hydroxybutyl)-1-methoximino-2-cyclopentene is prepared from 2-(3-carbethoxypropyl)-1-methoximino-2-cyclopentene and diisobutylaluminum hydride.

EXAMPLE 55

Preparation of 2-(6-carbethoxy-5-oxahexyl)-1-methoximino-2-cyclopentene

To an ice cold solution of 4.833 g. (0.0266 mole) of 2-(4-hydroxypentane)-1-methoximino-2-cyclopentene in 50 ml. of dry tetrahydrofuran under nitrogen is added 16.7 ml. of 1.6 molar n-butyl lithium in hexane, dropwise. The reaction mixture is stirred for 0.5 hour and then 4.85 g. (0.029 mole) of ethyl bromoacetate is added dropwise. The reaction mixture is stirred overnight at room temperature and then refluxed for 1.5 hours. The reaction is cooled and poured into water and extracted several times with ether. The ether extracts are washed with saline, dried over magnesium sulfate, and concentrated. The residue is placed on an alumina column, chloroform being used as a wash solvent. The combined washings are concentrated to dryness to give 4.903 g. of product as a yellow oil.

EXAMPLE 56

Preparation of 2-(6-carboxy-5-oxahexyl)-2-cyclopentenone

In the manner described in Example 26, treatment of 2-(carbethoxy-5-oxahexyl)-1-methoximino-2-cyclopentene with acetone and 2N hydrochloric acid at reflux gives the subject compound as a yellow oil.

EXAMPLE 57
Preparation of
2-(6-carbethoxy-5-oxahexyl)-2-cyclopentenone

In the manner described in Example 27, treatment of 2-(6-carboxy-5-oxahexyl)-2-cyclopentenone with p-toluenesulfonic acid in ethanol produces the subject product as a light yellow oil.

EXAMPLE 58
Preparation of
2-(4-p-toluenesulfonyloxybutyl)-1-methoxomino-2-cyclopentene In the manner described in Example 22, treatment of 2-(4-hydroxybutyl)-1-methoxyimino-2-cyclopentene with p-toluene sulfonyl chloride in pyridine gives the subject product as a light yellow oil; IR (film): 1600, 1190, 1050, 885 cm$^{-1}$.

EXAMPLE 59
Preparation of
2-(6-carbethoxy-5-thiahexyl)-1-methoximino-2-cyclopentene To a stirred mixture of 1.465 g. (0.0348 mole) of sodium hydride (57.2% in mineral oil) in 50 ml. of dimethoxyethane, under nitrogen, is added slowly 4.8 g. (0.0347 mole) of ethyl-2-mercaptoacetate. The reaction mixture is stirred at room temperature for one hour and then a solution of 7.8 g. (0.0231 mole) of 2-(4-p-toluenesulfonyloxybutyl)-1-methoximino-2-cyclopentene in 30 ml. of dimethoxyethane is added dropwise and stirred at room temperature for 18 hours. The solution is heated at reflux for one hour, cooled and poured into cold dilute hydrochloric acid and then extracted with ether. The combined ether extracts are washed with saline, dried over magnesium sulfate and evaporated to give 7.6 g. of subject product as a yellow oil.

EXAMPLE 60
Preparation of
2-(6-carboxy-5-thiahexyl)-2-cyclopentenone

In the manner described in Example 26, treatment of 2-(6-carbethoxy-5-thiahexyl)-1-methoximino-2-cyclopentene with acetone and 2N hydrochloric acid at reflux gives the subject product as a yellow oil.

EXAMPLE 61
Preparation of
2-(6-carbethoxy-5-thiahexyl)-2-cyclopentenone

In the manner described in Example 27 treatment of 2-(6-carboxy-5-thiahexyl)-2-cyclopentenone with p-toluenesulfonic acid in ethanol gives the subject ester as a yellow oil.

EXAMPLE 62
Preparation of
2-(6-carboxy-5-oxahexyl)-1-methoximino-2-cyclopentene To an ice cold solution of 3.66 g. (0.02 mole) of 2-(4-hydroxybutyl)-1-methoximino-2-cyclopentene (Example 54) in 50 ml. of 1,2-dimethoxyethane under nitrogen is added dropwise 17 ml. of 1.6 M n-butyl lithium in hexane. The reaction mixture is stirred for half an hour and then the lithium salt of chloroacetic acid, prepared from 1.89 g. (0.02 mole) of chloroacetic acid and 16 ml. of 1.6M n-butyl lithium in 20 ml. of dimethoxyethane, is added and the reaction mixture is heated at reflux for 48 hours. The solvent is evaporated and the residue is partitioned between ether and water. The aqueous phase is acidified with hydrochloric acid and extracted with ether. The organic phase is washed with water and saturated saline solution, dried (MgSO$_4$), and evaporated to give 3.35 g. of a yellow oil.

EXAMPLE 63
Preparation of
2-(6-carboxy-5-oxahexyl)-2-cyclopenten-1-one

In the manner described in Example 26, treatment of 2-(6-carboxy-5-oxahexyl)-1-methoximino-2-cyclopentene (Example 62) with acetone and 2N hydrochloric acid at reflux gives the subject compound as a yellow oil.

EXAMPLE 64
Preparation of
1-methoximino-2-(4-methanesulfonyloxybutyl)-2-cyclopentene To a solution of 1.83 g (0.01 mole) of 1-methoximino-2-(4-hydroxybutyl)-2-cyclopentene (Example 54) in 10 ml. of methylene chloride containing 1.52 g. (0.015 mole) of triethylamine is added 1.265 g. (0.011 mole) of methanesulfonyl chloride over a period of 5–10 minutes at 10°–0° C. Stirring is continued for 15 minutes and the solution is then washed with cold water, cold 10% hydrochloric acid, cold sodium bicarbonate solution, and cold saline solution. The organic phase is dried (MgSO$_4$) and concentrated to give an oil which solidifies upon cooling. Crystallization from ether-petroleum ether (30°–60° C.) gives 1.797 g. of white crystals, m.p. 67°–68° C.

EXAMPLE 65
Preparation of
1-methoximino-2-(5-cyanopentyl)-2-cyclopentene

A mixture of 2.75 g. (0.01 mole) of 1-methoximino-2-(5-methanesulfonyloxypentyl)-2-cyclopentene (Example 75) and 1.47 g. (0.03 mole) of sodium cyanide in 20 ml. of dry N,N-dimethylformamide is heated at 65°–70° C. for 3 hours. The cooled reaction mixture is poured into water and extracted with diethyl ether. The organic phase is washed with water and saturated saline solution, dried (MgSO$_4$), and evaporated to give 1.89 g. of a light yellow oil.

EXAMPLE 66
Preparation of
1-methoximino-2-(5-carboxypentyl)-2-cyclopentene

A mixture of 1.89 g (0.0092 mole) of 1-methoximino-2-(5-cyanopentyl)-2-cyclopentene (Example 65) and 1 g. (0.025 mole) of sodium hydroxide in 50 ml. of 1:1 aqueous-ethanol is refluxed for 48 hours, cooled, and partitioned between water and diethyl ether. The aqueous phase is acidified with hydrochloric acid, extracted with diethyl ether, and the organic phase is washed with water and saturated saline solution, dried (MgSO$_4$), and evaporated to give 1.86 g. of a yellow oil.

EXAMPLE 67
Preparation of 2-(5-carboxypentyl)-2-cyclopentenone

A solution of 1.86 g. (0.00825 mole) 1-methoximino-2-(5-carboxypentyl)-2-cyclopentene (Example 66) in 44 ml. of acetone and 13.1 ml. of 2N hydrochloric acid is refluxed for 5 hours. The solvent is partially evaporated and a solid precipitates and is collected. The residue is extracted with diethyl ether and the organic phase is washed with saturated saline solution, dried (MgSO$_4$), and evaporated to yield additional solid. The combined solid material is crystallized from ether/pet ether (30°–60° C) to yield crystalline material, m.p. 70°–72° C.

EXAMPLE 68

Preparation of
2-(5-carbethoxypentyl)-2-cyclopentenone

A solution of 1.309 g. (0.00668 mole) of 2-(5-carboxypentyl)-2-cyclopentenone (Example 67) and 90 mg. of p-toluenesulfonic acid in 150 ml. of ethanol is refluxed for 18 hours. The solvent is evaporated and the residue is dissolved in ether. The organic phase is washed with water, sodium bicarbonate solution, and saturated saline solution, dried (MgSO$_4$), and evaporated to give 1.371 g. of a light yellow oil.

EXAMPLE 69

Preparation of
2-(5-acetoxypentyl)-2-carbomethoxy/carbethoxy-cyclopentanone

A mixture of sodiocyclopentanone carboxylate, prepared from 1200 g. (8.0 moles) of cyclopentanone carboxylate (methyl and ethyl esters) and 200 g. (8.3 moles) of mineral oil free sodium hydride in 10.1 of 1,2-dimethoxyethane, 1320 g. (8.0 moles) of 5-chloro-1-amyl acetate [M. E. Synerholm, *Journ. Amer. Chem. Soc.*, 69, 2681 (1947)]; and 1200 g. (8.0 moles of sodium iodide is refluxed under nitrogen for 18 hours. The mixture is cooled, concentrated to 4.1 and partitioned between dilute hydrochloric acid and diethyl ether. The organic phase is washed with water and saturated brine, dried (MgSO$_4$), and evaporated to yield 1920 g. of an oil.

EXAMPLE 70

Preparation of
2-(5-hydroxypentyl)cyclopentanone/2-(5-acetoxypentyl)-cyclopentanone A mixture of 4,500 g. (16.2 moles) of 2-(5-acetoxypentyl)-2-carbomethoxy/carboethoxy-cyclopentanone (Example 69), 2.2 l. of glacial acetic acid, 1 l. of concentrated hydrochloric acid, and 1 l. of water is refluxed for 18 hours, cooled and partitioned between saturated brine and benzene. The organic phase is washed with saturated brine, dried (MgSO$_4$), and evaporated in vacuo to yield 3155 g. of an oil.

EXAMPLE 71

Preparation of
1-acetoxy-2-(5-acetoxypentyl)-1-cyclopentene

A solution of 400 g. (2.04 moles) of a mixture of 2-(5-hydroxypentyl)cyclopentanone and 2-(5-acetoxypentyl)cyclopentanone (Example 70) and 4.0 g. of p-toluenesulfonic acid monohydrate in 1 l. of acetic anhydride is refluxed at a rate to maintain a steady distillation of acetic acid from the reaction through a helix-packed fractionation column. The reaction is continued with the addition of acetic anhydride to maintain a constant volume until complete conversion of starting materials to product is evident. The mixture is cooled and partitioned between 2 l. of hexane and 3 l. of cold water containing solid sodium bicarbonate to maintain a neutral pH. The organic phase is washed with saturated brine, dried (MgSO$_4$), and evaporated to yield 452 g. of an oil.

EXAMPLE 72

Preparation of 2-(5-acetoxypentyl)-2-cyclopentenone

To a well stirred mixture of 405 g. (4.05 moles of calcium carbonate, 3 l. of water, and 2.5 l. of chloroform cooled to 5° C. is added simultaneously 1016 g. (4.0 moles) of 1-acetoxy-2-(5-acetoxy-pentyl)-1-cyclopentene (Example 71) and a solution of 648 g. (4.05 moles) of bromine in 500 ml. of carbon tetrachloride at a rate to maintain a temperature below 10° C. The mixture is stirred for half an hour after addition of the ragents and the phases are then separated. The organic phase is washed with 2% sodium thiousulfate solution, water, and saturated brine, dried (MgSO$_4$), and evaporated in vacuo to an oil. The oil is immediately added to a refluxing slurry of 500 g. (5.0 moles) of calcium carbonate in 2.5 l of N,N-dimethylacetamide under nitrogen and the mixture is then refluxed for thirty minutes. The mixture is cooled, filtered, and partitioned between water amd diethyl ether. The organic phase is washed with water and sarturated brine, dried (MgSO$_4$), and evaporated to yield 757 g. of an oil, b.p. 116°–118° C. (0.25 mm.).

EXAMPLE 73

Preparation of
1-methoximino-2-(5-acetoxypentyl)-2-cyclopentene

In the manner described for Example 20, 2-(5-acetoxypentyl)- 2-cyclopentenone (Example 72) is treated with methoxyamine hydrochloride in pyridine and ethanol to yield the subject compound, b.p. 101°–103° C. (0.20 mm.).

EXAMPLE 74

Preparation of
1-methoximino-2-(5-hydroxypentyl)-2-cyclopentene

A mixture of 74 mg. (0.22 mole) of 1-methoximino-2-(5-acetoxypentyl)-2-cyclopentene (Example 73) and 56 g. (1.0 mole of potassium hydroxide in 300 ml. of 1:1 aqueous methanol is refluxed for 2 hours and then cooled. The solvent is partially removed in vacuo and the residue is partitioned between saturated brine and diethyl ether. The organic phase is washed with saturated brine, dried (MgSO$_4$), and evaporated to yield an oil which crystallized, m.p. 35°–36° C.

EXAMPLE 75

Preparation of
1-methoximino-2-(5-methanesulfonyloxypentyl)-2-cyclopentene

To a cold solution of 9.85 g. (0.05 mole) of 1-methoximino-2-(5-hydroxypentyl)-2-cyclopentene (Example 74) and 7.6 g. (0.075 mole) of triethylamine in 100 ml. of methylene chloride at −10° C. is added 6.3 g. (0.055 mole) of methanesulfonyl chloride at a rate to maintain a temperature of −10° to 0° C. The mixture is then stirred for 15 minutes and the poured into ice water. The organic phase is washed with cold 10% hydrochloric acid, cold saturated sodium bicarbonate solution, and cold saturated brine, dried (MgSO$_4$), and evaporated to yield a solid, m.p. 78°–80° C.

EXAMPLE 76

Preparation of 1-methoximino-2-(6,6-dicarbethoxyhexyl)-2-cyclopentene

To a suspension of sodiodiethylmalonate in 1,2-dimethoxyethane, prepared from 248 g. (1.55 moles) of diethyl malonate and 1.72 g. (0.95 mole) of mineral oil free sodium hydride in 1 l. of 1,2-dimethoxyethane under nitrogen, is added 170 g. (0.62 mole) of 1-methoximino-2-(5-methanesulfonyloxypentyl)-2-cyclopentene (Example 75) in 1.5 l. of 1,2-dimethoxyethane and the mixture is refluxed for 5 hours. The mixture is cooled, filtered, and the solvent is evaporated. The residue is partitioned between cold dilute hydrochloric acid and water, and the organic phase is washed with saturated brine, dried ($MgSO_4$), and evaporated to remove solvent and excess diethyl malonate to yield 209 g. of an oil.

EXAMPLE 77

Preparation of 1-methoximino-2-(6,6-dicarboxyhexyl)-2-cyclopentene

In the manner described in Example 24, 1-methoximino-2-(6,6-dicarbethoxyhexyl)-2-cyclopentene is treated with potassium hydroxide in 1:1 aqeuous methanol and then hydrochloric acid to yield the desired compound as crystals from diethyl ether, m.p. 110°–115° C.

EXAMPLE 78

Preparation of 1-methoximino-2-(6-carboxyhexyl)-2-cyclopentene

A solution of 141 g. (0.50 mole) of 1-methoximino-2-(6,6-dicarboxyhexyl)-2-cyclopentene in 500 ml. of bis-(2-methoxyethyl) ether is refluxed for 2 hours, cooled, and evaporated to yield an oil. The latter is crystallized from hexane to yield 92 g. of solid, m.p. 70°–72° C.

EXAMPLE 79

Preparation of 2-(6-carboxyhexyl)-2-cyclopentenone

In the manner described in Example 26, treatment of 1-methoximino-2-(6-carboxyhexyl)-2-cyclopenten (Example 78) with acetone and 2N hydrochloric acid at reflux provides the subject compound.

EXAMPLE 80

Preparation of 2-(6-carbethoxyhexyl)-2-cyclopentenone

Fischer estification of 2-(6-carboxyhexyl)-2-cyclopentenone (Example 79) in the manner of Example 27 provides the subject compound.

EXAMPLE 81

Preparation of 1-methoximino-2-(6-fluoro-6,6-dicarbethoxyhexyl)-2-cyclopentene

To a solution of sodiodiethyl fluoromalonate, prepared from 2.062 g. (0.0491 mole) of sodium hydride in mineral oil (57.2%), 40 ml. of dry N,N-dimethylformamide and 8.174 g. (0.0458 mole) of diethyl fluoromalonate is added dropwise 11.32 g. (0.0413 mole) of 1-methoximino-2-(5-methylsulfonyloxypentyl)-2-cyclopentene (Example 75) in 60 ml. of N,N-dimethylformamide. The mixture is refluxed for 2 hours under a nitrogen atmosphere. The mixture is concentrated and partitioned between cold dilute hydrochloric acid and diethyl ether, and the organic phase is washed with saturated brine, dried ($MgSO_4$), and evaporated to yield 13.631 g. (92%) of a yellow oil.

EXAMPLE 82

Preparation of 1-methoximino-2-(6-fluoro-6,6-dicarboxyhexyl)-2-cyclopentene

A mixture of 13.631 g. of the diester of Example 81 and 16 g. of potassium hydroxide in 364 ml. of 1:1 aqueous methanol is refluxed for 5 hours, cooled, concentrated, and is partitioned between water and diethyl ether. The aqueous phase is acidified with hydrochloric acid, extracted with ether, and the organic phase is washed with saturated brine, dried ($MgSO_4$) and evaporated to yield a solid. The solid is crystallized from diethyl ether petroleum ether (30°–60° C.) to give 10 g. (90%) of white crystals, m.p. 143°–145° C. ($-CO_2$).

EXAMPLE 83

Preparation of 1-methoximino-2-(6-fluoro-6-carboxyhexyl)-2-cyclopentene

A solution of 10 g. of the diacid of Example 82 in 60 ml. of 2-methoxyethyl ether is refluxed for 7 hours, cooled, and evaporated to yield 8.5 g. (95%) of a tan solid. A sample is crystallized from diethyl ether-petroleum ether (30°–60° C.) to give white crystals, m.p. 98°–100° C.

EXAMPLE 84

Preparation of 2-(6-fluoro-6-carboxyhexyl)cyclopent-2-en-1-one

The acid methoxime (8.5 g.) from Example 83 is refluxed for 5 hours with 180 ml. of acetone and 84 ml. of 2N hydrochloric acid. The mixture is cooled, the solvent is evaporated, and the residue is partitioned between water and diethyl ether. The organic phase is washed with saturated brine, dried ($MgSO_4$) and evaporated to yield 7.4 g. (98%) of a light yellow oil.

EXAMPLE 85

Preparation of 2-(6-fluoro-6-carbethoxyhexyl)cyclopent-2-en-1-one

The acid ketone (7.4 g.) from Example 84 is Fisher esterified with 300 ml. of absolute ethanol and 400 mg. of p-toluenesulfonic acid for 18 hours, cooled, and the solvent is evaporated. The resulting oil is dissolved in ether, washed with dilute sodium bicarbonate solution, and saline, dried ($MgSO_4$), and evaporated to give 7.306 g. (86%) of a light yellow oil.

EXAMPLE 86

Preparation of 2-(7-cyanoheptyl)-1-methoximino-2-cyclopentene

Treatment of 1-methoximino-2-(7-p-toluenesulfonyloxy)-2-cyclopentene (Example 22) with sodium cyanide in the manner of Example 65 is productive of the subject compound.

EXAMPLE 87

Preparation of 2-(7-carboxyheptyl)-1-methoximino-2-cyclopentene

Alkaline hydrolysis of 2-(7-cyanoheptyl)-1-methoximino-2-cyclopentene (Example 86) by procedure of Example 66 is productive the subject compound.

EXAMPLE 88

Preparation of 2-(7-carboxyheptyl)-2-cyclopenten-1-one

Hydrolysis of the methoxime of Example 87 with acetone-hydrochloric acid by the procedure of Example 67 is productive of the subject compound.

EXAMPLE 89

Preparation of 2-(7-carbethoxyheptyl)-2-cyclopenten-1-one

Fisher esterification of the carboxylic acid of Example 88 by the procedure of Example 68 is productive of the subject compound.

EXAMPLE 90

Preparation of 2-(6,6-dicarbethoxy-6-phenylhexyl)-1-methoximino-2-cyclopentene

Treatment of 1-methoximino-2-(5-methanesulfonyloxypentyl)-2-cyclopentene (Example 75) with sodio diethyl phenylmalonate by the procedure of Example 76 is productive of the subject compound.

EXAMPLE 91

Preparation of 2-(6,6-dicarboxy-6-phenylhexyl)-1-methoximino-2-cyclopentene

Alkaline hydrolysis of 2-(6,6-dicarbethoxy-6-phenylhexyl)-1-methoximino-2-cyclopentene (Example 90) by the procedure of Example 24 is productive of the subject diacid.

EXAMPLE 92

Preparation of 2-(6-carboxy-6-phenylhexyl)-1-methoximino-2-cyclopentene

Decarboxylation of 2-(6,6-dicarboxy-6-phenylhexyl)-1-methoximino-2-cyclopentene (Example 91) by the procedure of Example 78 is productive of the subject compound.

EXAMPLE 93

Preparation of 2-(6-carboxy-6-phenylhexyl)-2-cyclopentene-1-one

Methoxime cleavage of 2-(6-carboxy-6-phenylhexyl)-1-methoximino-2-cyclopentene (Example 92) in the manner of Example 84 is productive of the subject ketone.

EXAMPLE 94

Preparation of 2-(6-carbethoxy-6-phenylhexyl)-2-cyclopenten-1-one

Fisher esterification of the carboxylic acid of Example 93 in the manner of Example 85 is productive of the subject keto-ester.

EXAMPLE 95

Preparation of 2-(6-fluoro-6,6-dicarbethocyhexyl)-1-methoximino-2-cyclopentene

An ethanolic solution of sodium ethoxide, prepared from 0.389 g. of sodium and 40 ml. of absolute ethanol, is treated at ambient temperatures with 5.05 g. of 2-(6,6-dicarbethoxyhexyl)-1-methoximino-2-cyclopentene (Example 76). The resulting solution is cooled to −20° C. and then treated with a stream of perchloryl fluoride until the mixture becomes neutral. The excess perchloryl fluoride is removed with a stream of nitrogen and the mixture is retreated with 10 ml. of an ethanolic solution of sodium ethoxide (from 0.350 g. of sodium) and then with perchloryl fluoride until the mixture becomes neutral. The excess perchloryl fluoride is removed with a stream of nitrogen and the mixture is filtered and evaporated to an oil. The latter is partitioned between ether and water and the organic phase is washed with saturated saline, dried ($Na_2SO_4$) and evaporated to afford the subject compound.

EXAMPLE 96

Preparation of 2-(4-bromobutyl)-1-methoximino-2-cyclopentene

A mixture of 15.24 g. of 2-(4-p-toluenesulfonyloxybutyl)-1-methoximino-2-cyclopentene (Example 58) and 10.70 g. of sodium bromide in 100 ml. of dimethylsulfoxide is stirred at ambient temperature for 48 hours and then poured into 600 ml. of water. The mixture is extracted with hexane and its organic phase is wasted with saturated brine, dried ($NaSO_4$), and evaporated to yield a tan oil.

EXAMPLE 97

Preparation of 2-(4-iodobutyl)-1-methoximino-2-cylopentene

To a solution of 1.5 g. of sodium iodide in 20 ml. of acetone is added 2.3 g. of 2-(4-bromobutyl)-1-methoximino-2-cyclopentene (Example 96) and the resulting mixture is stirred at ambient temperatures for 5 hours. The mixture is filtered and evaporated and the residue is partitioned between water and benzene. The organic phase is washed with saturated brine, dried ($NaSO_4$), and evaporated to yield a tan oil.

EXAMPLE 98

Preparation of 1-methoximino-2-(5-chloropentyl)-2-cyclopentene

A solution of 5 g. (0.0182 mole) of 2-(5-methylsulfonyloxypentyl)-2-cyclopentenone methoxime (Example 75) and 5 g. of lithium chloride in 100 ml. of N,N-dimethylformamide is heated at reflux for 1 hour. The solution is cooled and 100 ml. of water is added and extracted with diethyl ether. The combined extracts are washed with saline, dried ($MgSO_4$), and evaporated to yield a light yellow oil.

EXAMPLE 99

Preparation of 1-methoximino-2-(6,6-dicarbethoxyhexyl)cyclopent-2-ene

Treatment of 1-methoximino-2-(5-chlorophenyl)-2-cyclopentene (Example 98) with sodio diethylmalonate in the manner of Example 76 is productive of the subject compound.

EXAMPLE 100

Preparation of 1-methoximino-2-(5,5-dicarbethoxypentyl)-2-cyclopentene

Treatment of 2-(4-iodobutyl)-1-methoximino-2-cyclopentene (Example 97) or of 2-(4-bromobutyl)-1-methoximino-2-cyclopentene (Example 96) with sodio diethylmalonate in the manner of Example 76 is productive of the subject compound.

EXAMPLE 101

Preparation of 2-(6-carbo-n-butoxyhexyl)cyclopent-2-en-1-one

A solution of 50 g. of 2-(6-carboxyhexyl)cyclopent-2-en-1-one [Bagli et al., Tetrahedron Letters, No. 5, 465 (1966)]in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 102-104

Treatment of 2-(6-carboxyhexyl)cyclopent-2-en-1-one by the procedure of Example 101 with the appropriate alcohol affords the esters of the following table.

TABLE V

| Example | Alcohol | Product Ester |
| --- | --- | --- |
| 102 | isopropanol | 2-(6-carboisopropoxyhexyl)cyclopent-2-en-1-one |
| 103 | methanol | 2-(6-carbomethoxyhexyl)cyclopent-2-en-1-one |
| 104 | ethanol | 2-(6-carbethoxyhexyl)cyclopent-2-en-1-one |

EXAMPLE 105

Preparation of ethyl 9-oxoprostanoate

To a Grignard solution, prepared from 332 mg. of magnesium and 3.32 g. of n-octyl iodide in 10 ml. of diethyl ether under nitrogen atmosphere, is added 192 mg. of cuprous iodide-tris-n-butylphosphine complex followed by dropwise addition of 3 g. of 2-(6-carbethoxyhexyl)cyclopent-2-en-1-one and the resulting mixture is stirred for 2 hours. Saturated ammonium chloride (50 m.) is added followed by 25 ml. of water and 50 ml. of diethyl ether. The ether layer is washed successively with aqueous sodium thiosulfate solution, ammonium chloride solution, and water, dried with magnesium sulfate and taken to dryness leaving an oil. Distillation of 0.06 mm. of mercury (bath to 190° ) gives 2 g. of material containing unreacted starting material and 1.86 g. (42%) of residue which contains the desired product. This material is chromatographed on Florisil ®, an activated magnesium silicate. The product is eluted with 10% diethyl ether-in-hexane to give 737 mg. of an oil, which has no significant ultraviolet absorption; $\lambda_{max}^{KBr}$ 5.75, 8.50 $\mu$; nmr 2H quarter $\delta$ (OCH$_2$ of ester), 3H triplet 1.25 (CH$_3$ of ester), and 3H distorted triplet 0.91 (terminal methyl); mass spectrum: m/e 352; vapor phase chromatography shows one peak.

EXAMPLE 106

Preparation of isopropyl 9-oxo-19,20-bisnorprostanoate

By replacing the n-octyl iodide and 2-(6-carbethoxyhexyl)cyclopent-2-en-1-one employed in Example 105 with equimolecular quantities of n-hexyl bromide and 2-(6-carboisopropoxyhexyl)cyclopent-2-en-1-one, respectively, and following substantially the same procedure described in Example 105, there is obtained isopropyl 9-oxo-19,20-bisnorprostanoate.

EXAMPLE 107

Preparation of methyl 9-oxo-20-ethylprostanoate

The procedure of Example 105 is repeated, substituting equimolecular amounts of n-decyl chloride and 2-(6-carbomethoxyhexyl)cyclopent-2-en-1-one, respectively, for the n-octyl iodide and 2-(6-carbethoxyhexyl)cyclopent-2-en-1-one employed in that example. There is thus obtained methyl 9-oxo-20-ethylprostanoate.

EXAMPLE 108

Preparation of n-butyl 9-oxo-14,15,16,17,18,19,20-heptanorprostanoate

The procedure of Example 105 is repeated, substituting equimolecular amounts of methyl iodide and 2-(6-carbo-n-butoxyhexyl)cyclopent-2-en-1-one, respectively, for the n-octyl iodide and 2-(6-carboethoxyhexyl)cyclopent-2-en-1-one employed in that example. There is thus obtained n-butyl 9-oxo-14,15,16,17,18,19,20-heptanorprostanoate.

EXAMPLE 109

Preparation of n-butyl 9-oxo-18,19,20-trinorprostanoate

The procedure of Example 105 is repeated, substituting equimolecular amounts of n-amyl iodide and 2-(6-carbo-n-butoxyhexyl)cyclopent-2-en-1-one, respectively, for the n-octyl iodide and 2-(6-carboethoxyhexyl)cyclopent-2-en-1-one employed in that example. There is thus obtained n-butyl 9-oxo-18,19,20-trinorprostanoate.

EXAMPLE 110

Preparation of ethyl 9-oxo-17,18,19,20-tetranorprostanoate

The procedure of Example 105 is repeated, substituting an equimolecular amount of n-butyl iodide for the n-octyl iodide employed in that example. There is thus obtained ethyl 9-oxo-17,18,19,20-tetranorprostanoate.

EXAMPLE 111

Preparation of n-butyl 9-oxoprostanoate

The procedure of Example 105 is repeated, substituting an equimolecular amount of 2-(6-carbo-n-butoxyhexyl)cyclopent-2-en-1-one for the 2-(6-carboethoxyhexyl)cyclopent-2-en-1-one employed in that example. There is thus obtained n-butyl 9-oxoprostanoate.

EXAMPLE 112 preparation of ethyl 9-oxo-14,15,16,17,18,19,20-heptanorprostanoate

To a slurry of 38.09 g. (0.20 mole) of copper (I) iodide in 60 ml. of diethyl ether under nitrogen is added 238 ml. (0.39 mole) of 5.07% methyl lithium in ether maintaining a temperature −5° − −10° C. To the resulting solutin is added 23.83 g. (0.10 mole) of 2-(6-carboethoxyhexyl)-2-cyclopentenone and the mixture is stirred at −10° C. for 1 hour. The mixture is hydrolyzed with saturated ammonium chloride solution and the organic phase is separated, washed with water and saturated brine, dried ($Na_2SO_4$) and evaporaed to yield an oil. Distillation gives 23.4 g. of a colorless oil, b.p. 112°-115° C. (0.075 mm.) which by nmr consists of 85% trans isomer and 15% cis isomer. IR − 1745 $cm^{-1}$ (carbonyl) NMR: ($CDCl_3$) δ 0.90 doublet J=7.0 $H_2$ cis $CH-CH_3$; 1.17 doublet J = 5.5 $H_2$ trans $CH-CH_3$.

EXAMPLE 113

Preparation of 9-oxoprostanoic acid

A suspension of 300 mg. of ethyl 9-oxoprostanoate in 20 ml. of aqueous methanol (1:1) containing 300 mg. of potassium hydroxide is stirred at 50° C. for 1 hour and then at room temperature for 18 hours. The resulting solution is acidified with 1N hydrochloric acid, concentrated and extracted several times with diethyl ether. The combined ether extracts are washed with saturated sodium chloride solution, dried with anhydrous magnesium sulfate and taken to dryness to give 256 mg. (94%) of product as an oil; $\lambda_{max}$ 5.75, 5.85 μ; nmr 1H broad singlet δ 9.89 (carboxyl proton, exchangeable).

EXAMPLES 114-120

Saponification by the procedure of Example 113 of the alkyl esters indicated in the following table is productive of the prostanoic acids of the table.

TABLE VI

| Example | Starting Alkyl Prostanoate of | Product Prostanoic Acid |
|---|---|---|
| 114 | Example 106 | 9-Oxo-19,20-bisnorprostanoic acid |
| 115 | Example 107 | 9-Oxo-20-ethylprostanoic acid |
| 116 | Example 108 | 9-Oxo-14,15,16,17,18,19,20-heptanorprostanoic acid |
| 117 | Example 109 | 9-Oxo-18,19,20-trinorprostanoic acid |
| 118 | Example 110 | 9-Oxo-17,18,19,20-tetranorprostanoic acid |
| 119 | Example 111 | 9-Oxoprostanoic acid |
| 120 | Example 112 | 9-Oxo-14,15,16,17,18,19,20-heptanorprostanoic acid |

EXAMPLE 121

Preparation of the sodium salt of 3-(n-heptyl)-2-(6-carboxyhexyl)cyclopentanone

In 25 ml. of methanol was dissolved 3.06 g. of 3-(n-heptyl)-2-(6-carboxyhexyl)cyclopentanone and 0.54 g. of sodium methoxide and the resulting solution was evaporated to dryness. There was thus obtained the sodium salt as a white powder.

EXAMPLE 122

Preparation of the potassium salt of 3-(n-nonyl)-2-(6-carboxyhexyl)cyclopentanone In 25 ml. of water was dissolved 3.34 g. of 3-(n-nonyl)-2-(6-carboxyhexyl)cyclopentanone and 0.56 g. of pellet potassium hydroxide and the resulting solution was evaporated to dryness. There was thus obtained the potassium salt as an off white powder.

EXAMPLES 123-136

Treatment of the cyclopentenones of the following table with lithio dimethyl cuprate by the procedure described in Example 112 is productive of the 9-oxo-14,15,16,17,18,19,20-heptanorprostanoate esters [3-methyl-2-(ω-carbalkoxycyclopentanones] of the table.

TABLE VII

| Example | Starting Alkyl Cyclopentenone Ester of | Product 9-Oxo-prostanoate Ester |
|---|---|---|
| 123 | Example 19 | Ethyl 9-Oxo-6,7,14,15,16,17,18,19,20-Nonanorprostanoate |
| 124 | Example 27 | Ethyl 9-Oxo-7a,7b-bishomo-14,15,16,17,18,19,20-heptanorprostanoate |
| 125 | Example 42 | Ethyl 9-Oxo-2-ethyl-14,15,16,17,18,19,20-heptanorprostanoate |
| 126 | Example 52 | Ethyl 9-Oxo-3,3-dimethyl-14,15,16,17,18,19,20-heptanorprostanoate |
| 127 | Example 57 | Ethyl-9-Oxo-3-oxa-14,15,16,17,18,19,20-heptanorprostanoate |
| 128 | Example 61 | Ethyl 9-Oxo-3-thia-14,15,16,17,18,19,20-heptanorprostanoate |
| 129 | Example 68 | Ethyl 9-Oxo-7,14,15,16,17,18,19,20-octanorprostanoate |
| 130 | Example 18 | Ethyl 9-Oxo-5,6,7,14,15,16,17,18,19,20-decanorprostanoate |
| 131 | Example 85 | Ethyl 9-Oxo-2-fluoro-14,15,16,17,18,19,20-heptanorprostanoate |
| 132 | Example 89 | Ethyl 9-Oxo-7a-homo-14,15,16,17,18,19,20-heptanorprostanoate |
| 133 | Example 94 | Ethyl 9-Oxo-2-phenyl-14,15,16,17,18,19,20-heptanorprostanoate |
| 134 | Example 101 | Butyl 9-Oxo-14,15,16,17,18,19,20-heptanorprostanoate |
| 135 | Example 102 | Isopropyl 9-Oxo-14,15,16,17,18,19,20-heptanorprostanoate |
| 136 | Example 103 | Methyl 9-Oxo-14,15,16,17,18,19,20-heptanorprostanoate |

EXAMPLE 137

Preparation of 9-oxo-15,16,17,18,19,20-hexanorprostanoate

A Grignard solution, prepared under nitrogen atmosphere at 45°-50° C. from 535 mg. of magnesium and 3.44 g. of ethyl iodide in 8 ml. of toluene containing 1 mole of tetrahydrofuran per gram atom of magnesium, is added dropwise with stirring to a solution of 4.766 g. of 2-(6-carbethoxyhexyl)2-cyclopentenone in 40 ml. of tetrahydrofuran containing 330 mg. of cuprous iodide-tris-n-butylphosphine complex in the cold. The resulting solution is stirred at room temperature for 1 hour and then is poured into cold dilute hydrochloric acid and extracted with ether. The combined extracts are washed with saline solution, dried over magnesium sulfate and evaporated to give 5.14 g. of an oil. The crude oil is dissolved in ether and treated with four equivalents of aqueous potassium permanganate for 10 minutes. The mixture is filtered and the filtrate is washed with saline, dried over magnesium sulfate and evaporated. This residual material is further purified by silica gel chromatography to give 2.1 g. of a light yellow oil, IR 1740 $cm^{-1}$ (ester and carbonyls).

EXAMPLES 138-154

Treatment of the cyclopentenones of the following table by the procedure described in Example 137 with the indicated Grignard reagent, prepared as required from ethyl iodide, propyl iodide, isopropyl iodie or butyl iodide in the manner of Example 137, is productive of the alkyl 9-oxoprostanoates of the table.

TABLE VIII

| Ex. | Starting Cyclopentenone Ester of | Grignard Reagent | Product 9-Oxoprostanoate Ester |
|---|---|---|---|
| 138 | Example 103 | $C_2H_5MgI$ | Methyl 9-Oxo-15,16,17,18,19,20-hexanorprostanoate |
| 139 | Example 17 | isopropyl-MgI | Ethyl 9-Oxo-13-methyl-15,16,17,18,19,20-hexanorprostanoate |
| 140 | Example 17 | propyl-MgI | Ethyl 9-Oxo-16,17,18,19,20-pentanorprostanoate |
| 141 | Example 19 | $C_2H_5MgI$ | Ethyl 9-Oxo-6,7,15,16,17, |

TABLE VIII-continued

| Ex. | Starting Cyclopentenone Ester of | Grignard Reagent | Product 9-Oxoprostanoate Ester |
|---|---|---|---|
| 142 | Example 19 | propyl-MgI | Ethyl 9-Oxo-6,7,16,17,18,19,20-heptanorprostanoate |
| 143 | Example 27 | $C_2H_5MgI$ | Ethyl 9-Oxo-7a,7b-bishomo-15,16,17,18,19,20-hexanorprostanoate |
| 144 | Example 42 | $C_2H_5MgI$ | Ethyl 9-Oxo-2-ethyl-15,16,17,18,19,20-hexanorprostanoate |
| 145 | Example 52 | $C_2H_5MgI$ | Ethyl 9-Oxo-3,3-dimethyl-15,16,17,18,19,20-hexanorprostanoate |
| 146 | Example 52 | propyl-MgI | Ethyl 9-Oxo-3,3-dimethyl-16,17,18,19,20-pentanorprostanoate |
| 147 | Example 68 | $C_2H_5MgI$ | Ethyl 9-Oxo-7,15,16,17,18,19,20-heptanorprostanoate |
| 148 | Example 68 | propyl-MgI | Ethyl 9-Oxo-7,16,17,18,19,20-hexanorprostanoate |
| 149 | Example 85 | $C_2H_5MgI$ | Ethyl 9-Oxo-2-fluoro-15,16,17,18,19,20-hexanorprostanoate |
| 150 | Example 85 | propyl-MgI | Ethyl 9-Oxo-2-fluoro-16,17,18,19,20-pentanorprostanoate |
| 151 | Example 89 | $C_2H_5MgI$ | Ethyl 9-Oxo-7a-homo-15,16,17,18,19,20-hexanorprostanoate |
| 152 | Example 19 | butyl-MgI | Ethyl 9-Oxo-6,7,17,18,19,20-hexanorprostanoate |
| 153 | Example 52 | butyl-MgI | Ethyl 9-Oxo-3,3-dimethyl-17,18,19,20-tetranorprostanoate |
| 154 | Example 85 | butyl-MgI | Ethyl 9-Oxo-2-fluoro-17,18,19,20-tetranorprostanoate |

EXAMPLE 155

Preparation of ethyl 9-oxo-18,19,20-trinorprostanoate

A mixture of 2 g. (6.49 mmoles) of ethyl 9-oxo-18,19,20-trinor-13-prostenoate (Example 30) 1 g. of 10% palladium-in-charcoal in 50 ml. of ethanol is shaken in a Parr low pressure hydrogenation apparatus at an initial hydrogen pressure of 30 psi until hydrogen uptake ceased. The reaction mixture is filtered and concentrated. The residue is dissolved in ether, washed with saline solution, dried over magnesium sulfate and concentrated to give 1.94 g. of a light yellow oil, IR 1740 cm$^{-1}$ (ester and ketone carbonyls).

EXAMPLES 156–184

Saponification of the 9-oxoprostanoate esters of the following table by the procedure of Example 113 is productive of the prostanoic acids of the table.

TABLE IX

| Examples | Starting 9-Oxoprostanoate Ester of Example No. | Product 9-Oxo-prostanoic Acid |
|---|---|---|
| 156 | 123 | 9-Oxo-6,7,14,15,16,17,18,19,20-nonanorprostanoic Acid |
| 157 | 124 | 9-Oxo-7a,7b,bishomo-14,15,16,17,18,19,20-heptanorprostanoic Acid |
| 158 | 125 | 9-Oxo-2-ethyl-14,15,16,17,18,19,20-heptanorprostanoic Acid |
| 159 | 126 | 9-Oxo-3,3-dimethyl-14,15,16,17,18,19,20-heptanorprostanoic Acid |
| 160 | 127 | 9-Oxo-3-oxa-14,15,16,17,18,19,20-heptanorprostanoic Acid |
| 161 | 128 | 9-Oxo-3-thia-14,15,16,17,18,19,20-heptanorprostanoic Acid |
| 162 | 129 | 9-Oxo-7,14,15,16,17,18,19,20-octanorprostanoic Acid |
| 163 | 130 | 9-Oxo-5,6,7,14,15,16,17,18,19,20-decanorprostanoic Acid |
| 164 | 131 | 9-Oxo-2-fluoro-14,15,16,17,18,19,20-heptanorprostanoic Acid |
| 165 | 132 | 9-Oxo-7a-homo-14,15,16,17,18,19,20-heptanorprostanoic Acid |
| 166 | 133 | 9-Oxo-2-phenyl-14,15,16,17,18,19,20-heptanorprostanoic Acid |
| 167 | 137 | 9-Oxo-15,16,17,18,19,20-hexanorprostanoic Acid |
| 168 | 139 | 9-Oxo-13-methyl-15,16,17,18,19,20-hexanorprostanoic Acid |
| 169 | 140 | 9-Oxo-16,17,18,19,20-pentanorprostanoic Acid |
| 170 | 141 | 9-Oxo-6,7,15,16,17,18,19,20-octanorprostanoic Acid |
| 171 | 142 | 9-Oxo-6,7,16,17,18,19,20-heptanorprostanoic Acid |
| 172 | 143 | 9-Oxo-8a,7b-bishomo-15,16,17,18,19,20-hexanorprostanoate Acid |
| 173 | 144 | 9-Oxo-2-ethyl-15,16,17,18,19,20-hexanorprostanoic Acid |
| 174 | 145 | 9-Oxo-3,3-dimethyl-15,16,17,18,19,20-hexanorprostanoic Acid |
| 175 | 146 | 9-Oxo-3,3-dimethyl-16,17,18,19,20-pentanorprostanoic Acid |
| 176 | 147 | 9-Oxo-7,15,16,17,18,19,20-heptanorprostanoic Acid |
| 177 | 148 | 9-Oxo-7,16,17,18,19,20-hexanorprostanoic Acid |
| 178 | 149 | 9-Oxo-2-fluoro-15,16,17,18,19,20-hexanorprostanoic Acid |
| 179 | 150 | 9-Oxo-2-fluoro-16,17,18,19,20-pentanorprostanoic Acid |
| 180 | 151 | 9-Oxo-7a-homo-15,16,17,18,19,20-hexanorprostanoic Acid |
| 181 | 152 | 9-Oxo-6,7,17,18,19,20-hexanorprostanoic Acid |
| 182 | 153 | 9-Oxo-3,3-dimethyl-17,18,19,20-tetraprostanoic Acid |
| 183 | 154 | 9-Oxo-2-fluoro-17,18,19,20-tetranoroprostanoic Acid |
| 184 | 155 | 9-Oxo-18,19,20-trinorprostanoic Acid |

EXAMPLE 185

Preparation of Ethyl 9-oxo-10a-homo-14,15,16,17,18,19,20-heptanorprostanoate

Treatment of ethyl 7-(cyclohex-2-en-1-one-2-yl)-heptanoate (Example 28) with lithio dimethyl cuprate in the manner of Example 112 is productive of the subject compound.

EXAMPLE 186

Preparation of 9-oxo-10a-homo-14,15,16,17,18,19,20-heptanorprostanoic Acid

Saponification of ethyl 9-oxo-10a-homo-14,15,16,17,18,19,20-heptanorprostanoate (Example 185) by the procedure of Example 113 is productive of the subject prostanoic acid.

EXAMPLE 187

Preparation of diethyl (5-chloro-1,1-dimethylpentyl)malonate

Magnesium (71 g. 2.92 moles) in 1 l. of ether containing a few crystals of iodine is added dropwise to 1-chloro-4-bromobutane (500 g., 2.92 moles) over a period of 30 minutes with stirring under nitrogen. The reaction is maintained at a temperature of 0° C. to 5° C. by immersing in an acetone-Dry Ice bath periodically. After stirring for 30 minutes at room temperature, the solution is chilled to below 0° C. and is then transferred to a dropping funnel from which it is added dropwise to diethyl isopropylidene malonate (440 g., 2.19 moles) [A. C. Cope and E. M. Hancock, Jour. Amer. Soc., 60, 2644 (1938)] dissolved in 1000 ml. of ether containing the tri(n-butyl)phosphine complex of copper (I) iodide (57 g.) [G. B. Kaufman and L. A. Teter, Inorganic Synthesis, 7, 9(1963)] at −10° C. with stirring under nitrogen over a period of two hours. After stirring at room temperature for 4 hours, the reaction mixture is poured into cold dilute hydrochloric acid and is extracted with ether. The combined ether extracts are washed with saline solution, dried over magnesium sulfate, and concentrated in vacuo to give 700 g. of crude amber oil, which is distilled under vacuum to yield two fractions: 212.4 g. with b.p. at 110° C–135° C. at 0.3 mm. and 100.0 g. with b.p. at 135° C.–145° C. at 0.3 mm. The total yield is 312.4 g. (49%).

EXAMPLE 188

Preparation of 3,3-dimethyl-7-chloroheptanoic acid

A mixture containing diethyl 5-(5-chloro-1,1-dimethylpentyl)malonate (648 g., 2.22 moles) potassium hydroxide (460 g.) and eight liters of 1:1 isopropanol:water is stirred at room temperature overnight. Most of the isopropanol is distilled and the residue is diluted with water, and then carefully acidified with conc. hydrochloric acid. The mixture is extracted with ether and the extracts are washed with water and saline, dried over magnesium sulfate and concentrated in vacuo to give 548 g. of crude oil. The oil is dissolved in three liters of diglyne which is heated under reflux for sixteen hours. About 2.7 l. of solvent is distilled, and the remainder is diluted with water and extracted with ether. The extracts are washed with saline, dried over magnesium sulfate and concentrated in vacuo to give 428 g. of crude oil (99%).

EXAMPLE 189

Preparation of ethyl 3,3-dimethyl-7-chloroheptanoate

To a solution of 3,3-dimethyl-7-chloroheptanoic acid (428 g., 2.21 moles) in 3 l. of chloroform containing 3 ml. of N,N-dimethylformamide is added 500 ml. of thionyl chloride and the resulting solution is tested under reflux for 3 hours. The reaction solution then is concentrated in vacuo and the residual acid chloride is dissolved in a minimum amount of benzene and added slowly to a solution containing 1260 ml. of 95% ethanol and 2520 ml. of benzene and 390 ml. of collidine. After heating under reflux for one hour, the solution is concentrated and the residue is dissolved in ether washed with water, dilute sodium bicarbonate solution and saline solution, dried over magnesium sulfate and concentrated to give 415 g. of crude oil, which is distilled under vacuum to yield two fractions: 46.6 g. boiling at 75° C. (0.3 mm.) and 236.7 g. boiling at 75° C. − 80° C. (0.3 mm). The total yield is 283.3 g. (60%) and the product is indicated to be 95% pure by g.l.c.

EXAMPLE 190

Preparation of methyl/ethyl 2-(6-carbethoxy-5,5-dimethylhexyl)cyclopentanone-2-carboxylate Sodium hydride (67 g., 1.55 moles) is placed in a three l. round-bottom flask and to this is added 1.1 liters of glyme from a dropping funnel under nitrogen flow and with stirring. To the resulting grayish mixture is added the 2-carbalkoxycyclopentanone (mixed methyl and ethyl esters) dropwise over a period of 45 minutes with nitrogen flow whilst the temperature is maintained in the range of 40°–55°. Ethyl 3,3-dimethyl-7-chloroheptanoate (283 g., 1.28 moles) and potassium iodide (195 g., 1.32 moles) are added and the mixture is heated at reflux overnight. After most of the solvent is distilled, the residue is made acidic with dilute hydrochloric acid and is then extracted with ether. The ether extracts are washed with water and saline solution, dried over magnesium sulfate, and concentrated in vacuo to 500 g. of crude yellow oil, which is distilled to give 405 g. (94% yield) of oil with b.p. 140°–180° (0.8 mm).

EXAMPLE 191

Preparation of 7-(2-Cyclopentanone)-3,3 dimethylheptanoic acid

Methyl/Ethyl 2-(6-carbethoxy-5,5-dimethylhexyl)-cyclopentanone-2-carboxylate (200 g., 0.6 moles), glacial acetic acid (180 ml) and 240 ml. of diluted hydrochloric acid, prepared from 100 ml. of conc. hydrochloric acid and 300 ml. of water, are placed in a 2 l. flask, containing a reflux condenser and a magnetic stirrer. The mixture then is stirred at reflux for 24 hours. The reaction mixture is cooled, 1 l. of water is added and the mixture is extracted several times with benzene. The organic extracts are combined, washed with saturated sodium chloride solution, dried over magnesium sulfate, filtered and concentrated to an oil (173.5 g.). The oil is rendered basic with sodium hydroxide solution, extracted with benzene and made acidic with hydrochloric acid and reextracted with benzene several times. The benzene layers are combined and washed with water, saturated sodium chloride solution, dried over magnesium sulfate, filtered and concentrated to yield 109.8 g. (78%) of crude oil, which was used without further purification in the next step.

EXAMPLE 192

Preparation of Ethyl 7-(2-Cyclopentanone)-3,3-dimethylheptanoate

To a solution of 7-(2-cyclopentanone)-3,3-dimethylheptanoic acid (45 g., 0.22 mol.) in 285 ml. of chloroform containing three drops of N,N-dimethylformamide is added dropwise 25 ml. of thionyl chloride. The solution is stirred at room temperature for 20 minutes, the solvent is removed at reduced pressure and the residual acid chloride is dissolved in a minimum amount of benzene and added slowly to a solution containing 115 ml. of ethanol, 230 ml. benzene and 30 ml. of collodine. This solution is heated under reflux for 15 minutes and then concentrated. The residue is dissolved in ether, washed with water, diluted sodium bicarbonate solution and saline solution, dried over magnesium sulfate and concentrated to give 51 g. of crude oil. Distillation gives 40 g. (67%) b.p. 135°–145° (0.1 mm.) of oil.

EXAMPLE 193

Preparation of 1-Acetoxy-2-(6-carbethoxy-5,5-dimethylhexyl)cyclopent-1-ene

A solution of ethyl 7-(2-cyclopentanone)-3,3-dimethylheptanoate (90 g., 0.336 mol.) and p-toluenesulfonic acid (0.94 g.) in 250 ml. of acetic anhydride is heated to boiling under partial reflux, allowing distillate at 118° or less (i.e. acetic acid) to escape then a vigreux column equipped with a condenser to collect the distillate. After 10 hours 130 ml. of distillate is collected. Another 50 ml. of acetic anhydride is added and the reaction is heated for 5 more hours; an additional 125 ml. of acetic anhydride is added, the reaction is heated for 7 more hours; finally another 50 ml. of acetic anhydride is added and heating is continued for 4 more hours. The solution is cooled and poured (cautiously) into a cold (0°–5°) mixture of saturated aqueous sodium bicarbonate (400 ml.) and hexane (250 ml.). The resulting cold mixture is stirred for 30 minutes during which time portions of solid sodium bicarbonate are added periodically until carbon dioxide evalution ceases. The hexane layer is separated and washed with saturated sodium chloride solution until the washings are neutral, dried over magnesium sulfate and treated with Darco decolorizing charcoal for clarification and then evaporated to dryness leaving an amber colored oil (87.5 g., 84%).

EXAMPLE 194

Preparation of 2-(6-Carboxy-5,5-dimethylhexyl)cyclopent-2-en-1-one

To a rapidly stirred mixture of 1-acetoxy-2-(6-carbethoxy-5,5-dimethylhexyl)cyclopent-1-ene (35 g., 0.113 mole) chloroform (95 ml.), water (125 ml.) and calcium carbonate (11.8 g.) cooled in an ice-bath is added dropwise over a period of thirty minutes a solution of bromine (18.8 g.) in carbon tetrachloride (31 ml.). After stirring in the cold for an additional 45 minutes the orange colored chloroform layer is separated and washed with dilute sodium bisulfite and saturated saline solution, dried over magnesium sulfate and taken to dryness in vacuo (bath temperature: 35°–40°) leaving an amber colored oil. A slurry of 100 ml. of N,N-dimethylacetamide and 16.5 g. of $CaCO_3$ is stirred and heated to reflux under nitrogen flow. The above dried oil is added from a dropping funnel rapidly, maintaining reflux and nitrogen flow for thirty minutes. The cooled reaction mixture is filtered, and the precipitate is washed with ether. The filtrate is poured into two liters ice-cold water and is extracted with ether. The combined extracts and washing is washed with water, saturated saline, treated with decolorizing charcoal, filtered. The solvent evaporated in vacuo to give 24 g. (77%) of subject product.

We claim:

1. A compound selected from the group consisting of those of the formula:

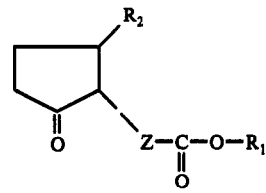

wherein $R_1$ is hydrogen or alkyl having up to four carbon atoms; $R_2$ is a straight chain alkyl group having from one to ten carbon atoms, inclusive; and Z is a divalent radical of the formulae:

$-(CH_2)_n-O-CH_2-$, $-(CH_2)_n-S-CH_2-$ or

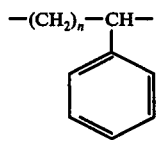

wherein n is an integer from three to five, inclusive; the stereoisomers thereof; and the cationic salts thereof when $R_1$ is hydrogen.

2. A compound according to claim 1 wherein $R_1$ is ethyl, $R_2$ is methyl, and Z is $-(CH_2)_4-O-CH_2-$.

3. A compound according to claim 1 wherein $R_1$ is ethyl, $R_2$ is methyl, and Z is $-(CH_2)_4-S-CH_2-$.

4. A compound according to claim 1 wherein $R_1$ is ethyl, $R_2$ is methyl, and Z is

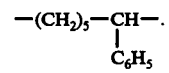

5. A compound according to claim 1 wherein $R_1$ is hydrogen, $R_2$ is methyl, and Z is $-(CH_2)_4-O-CH_2-$.

6. A compound according to claim 1 wherein $R_1$ is hydrogen, $R_2$ is methyl, and Z is $-(CH_2)_4-S-CH_2-$.

7. A compound according to claim 1 wherein $R_1$ is hydrogen, $R_2$ is methyl, and Z is

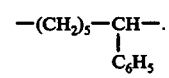

8. A compound according to claim 1 wherein $R_1$ is hydrogen, $R_2$ is n-octyl, and Z is $-(CH_2)_4-S-CH_2-$.

9. A compound according to claim 1 wherein $R_1$ is methyl, $R_2$ is n-octyl, and Z is $-(CH_2)_4-S-CH_2-$.

10. A compound according to claim 1 wherein $R_1$ is ethyl, $R_2$ is n-octyl, and Z is $-(CH_2)_4-S-CH_2-$.

* * * * *